(12) United States Patent
Sanders et al.

(10) Patent No.: US 6,171,559 B1
(45) Date of Patent: Jan. 9, 2001

(54) TOOTHBRUSH STERILIZATION UNIT FOR HOME USE

(76) Inventors: Marcia Sanders; Daniel Sanders, both of 200 W. 57th St., New York, NY (US) 10019

( * ) Notice: Under 35 U.S.C. 154(b), the term of this patent shall be extended for 0 days.

(21) Appl. No.: 09/468,659

(22) Filed: Dec. 21, 1999

(51) Int. Cl.[7] ....................................................... A61L 2/00
(52) U.S. Cl. ...................... 422/300; 134/144; 422/292; 422/297; 422/305
(58) Field of Search .................... 422/292, 297, 422/300, 305; 134/144

(56) References Cited

U.S. PATENT DOCUMENTS

| | | |
|---|---|---|
| 3,810,479 | 5/1974 | Miles . |
| 4,625,119 | 11/1986 | Murdock . |
| 4,740,706 | 4/1988 | Murdock . |
| 4,759,383 | 7/1988 | Phillips . |
| 4,816,648 | 3/1989 | Dusbabek . |
| 4,973,847 | 11/1990 | Lackey et al. . |
| 5,029,252 | 7/1991 | Ameseder . |
| 5,061,106 | 10/1991 | Kent . |
| 5,166,528 | 11/1992 | Levay . |
| 5,487,877 | 1/1996 | Choi . |
| 5,699,575 | 12/1997 | Peifer . |
| 5,919,416 | 7/1999 | Auner . |
| 5,920,075 | 7/1999 | Whitehead . |
| 5,935,537 | 8/1999 | Schad ................................... 422/300 |
| 5,979,472 | 11/1999 | Lowery et al. ..................... 134/58 R |

Primary Examiner—Krisanne Thornton

(57) ABSTRACT

A toothbrush sterilization unit for sterilizing the bristle-head of at least one toothbrush with a disinfectant. The toothbrush sterilization unit includes a housing having an interior compartment. The interior compartment includes a plurality of docking stations for holding in place a plurality of toothbrushes. The housing includes a pumping system assembly for dispensing a disinfectant on the bristle-heads of the toothbrushes during a dispensing cycle. The housing also includes a rotary fan and a heating member for drying the disinfectant on the bristle-heads of the plurality of toothbrushes during a drying cycle.

42 Claims, 16 Drawing Sheets

content truncated …

TOOTHBRUSH STERILIZATION UNIT FOR HOME USE

FIELD OF THE INVENTION

This invention relates to a unique sterilization system for sterilizing toothbrushes. More particularly, the sterilization system incorporates a hot air drying device to be used in conjunction with an anti-microbial spray to effectively sterilize and hold multiple manual toothbrushes or detachable toothbrush heads of electric toothbrushes in an ergonomically designed holder having a plurality of docking stations therein.

BACKGROUND OF THE INVENTION

Medical studies have indicated that unsterile toothbrushes may be contributing factors to lingering sore throats, bacterial and viral infections, as well as a physical carrier to the spread of these diseases, and periodontal disease. New toothbrushes have been found to contain bacteria on their bristles, such that the frequent replacement of a toothbrush may not obviate the problem of bacterial contamination or the spread of diseases to the user.

There remains a need for a sterilization system for sterilizing one or more toothbrushes that incorporates a hot air drying device to be used in conjunction with an anti-microbial spray. Additionally, the sterilization system should include an ergonomically designed holder having a plurality of docking stations therein for use on a wall or countertop. Further, the anti-microbial spray should be administered automatically or manually onto the bristle section of the toothbrush.

DESCRIPTION OF THE PRIOR ART

Sterilization devices, units or systems using various sterilizing methods to decontaminate toothbrushes are well known in the art. These sterilization devices having various designs, configurations, structures and materials of construction have been disclosed in the prior art. For example, U.S. Pat. No. 5,919,416 to Auner discloses an apparatus to sterilize toothbrushes with boiling water within a sterilization tray by using microwave energy. This apparatus does not disclose or teach the structure, configuration, design or method of the present invention of a toothbrush sterilization unit for home use.

U.S. Pat. No. 4,816,648 to Dusbabek discloses a toothbrush sterilizer having a housing with an interior sterilization cavity or well formed therein for allowing the bristle portion of the toothbrush to be inserted within the cavity. The toothbrush sterilizer further includes a heating element in combination with a heat transfer element, and when activated causes the sterilization cavity to be dry heated a sufficient amount to sterilize the toothbrush bristles of the toothbrush positioned within the sterilization cavity. This toothbrush sterilizer does not disclose or teach the structure, configuration, design or method of the present invention of a toothbrush sterilization unit for home use.

U.S. Pat. No. 4,759,383 to Phillips discloses a toothbrush sterilizing device that includes a housing having a top compartment and a bottom compartment. The top compartment includes a sterilizing solution therein for sterilizing a toothbrush. This toothbrush sterilizing device does not disclose or teach the structure, configuration, design or method of the present invention of a toothbrush sterilization unit for home use.

U.S. Pat. Nos. 5,920,075; 5,487,877; 5,166,528; 5,029,252; 4,973,847; 4,740,706; and 4,625,119 all disclose various devices for sterilizing the bristles of toothbrushes using U-V lamps or germicidal lamps in order to destroy the bacteria on the bristles of the toothbrushes. These aforementioned devices do not disclose or teach the structure, configuration, design or method of the present invention of a toothbrush sterilization unit for home use.

None of the aforementioned prior art patents teach or disclose the combination of features of an automatic or manually applied disinfectant spray with a hot air drying system for sterilizing the toothbrush where the housing of the toothbrush sterilization unit includes a plurality of docking stations for multiple toothbrushes as shown in the present invention. Additionally, no single patent teaches or discloses the structure, configuration, design and method of operation of the toothbrush sterilization unit of the present invention.

Accordingly, it is an object of the present invention to provide a toothbrush sterilization system that incorporates a hot air drying device to be used in conjunction with an anti-microbial spray to effectively sterilize and hold multiple toothbrushes in an ergonomically designed toothbrush holder having a plurality of docking stations therein for use on a wall or counter-top.

Another object of the present invention is to provide a toothbrush sterilization system that would administer the anti-microbial spray onto the bristle section of the toothbrush automatically or manually in order to decontaminate the toothbrush bristles.

Another object of the present invention is to provide a toothbrush sterilization system having a docking station for receiving a toothbrush, and an automatic switch for activating a hot air drying device that would effectively dry the disinfectant spray on the bristle-head of the toothbrush.

Another object of the present invention is to provide a toothbrush sterilization system that includes a light indicator by each docking station which signals the user when each toothbrush has dried the disinfectant spray and is ready for reuse.

Another object of the present invention is to provide a toothbrush sterilization system that includes numbered or color coded docking stations, such that the toothbrush remains in its docking station protected from any airborne bacteria and separated from toothbrushes of other family members which would be contained within their own coded docking stations.

Another object of the present invention is to provide a toothbrush sterilization system that contains voice recognition capabilities to tell each user which toothbrush is theirs when any given toothbrush is removed from its personal docking station.

Another object of the present invention is to provide a toothbrush sterilization system that is battery operated for portability.

Another object of the present invention is to provide a toothbrush sterilization system that is light-weight, easy to clean, made from durable plastics or metals, and is easy to use by the consumer.

A further object of the present invention is to provide a toothbrush sterilization system that can be mass produced in an automated and economical manner and is readily affordable by the consumer.

SUMMARY OF THE INVENTION

In accordance with the present invention, there is provided a toothbrush sterilization unit for sterilizing the bristle-head of at least one toothbrush with a disinfectant. The toothbrush sterilization unit includes a housing having an interior compartment. The interior compartment includes a plurality of docking stations for holding in place a plurality of toothbrushes. The housing includes a pumping system assembly for dispensing a disinfectant on the bristle-heads of the toothbrushes during a dispensing cycle. The housing also includes a rotary fan and a heating member for drying the disinfectant on the bristle-heads of the plurality of toothbrushes during a drying cycle.

BRIEF DESCRIPTION OF THE DRAWINGS

Further objects, features, and advantages of the present invention will become apparent upon the consideration of the following detailed description of the presently-preferred embodiment when taken in conjunction with the accompanying drawings, wherein.

DETAILED DESCRIPTION OF THE PREFERRED EMBODIMENT 10

Figure 1:
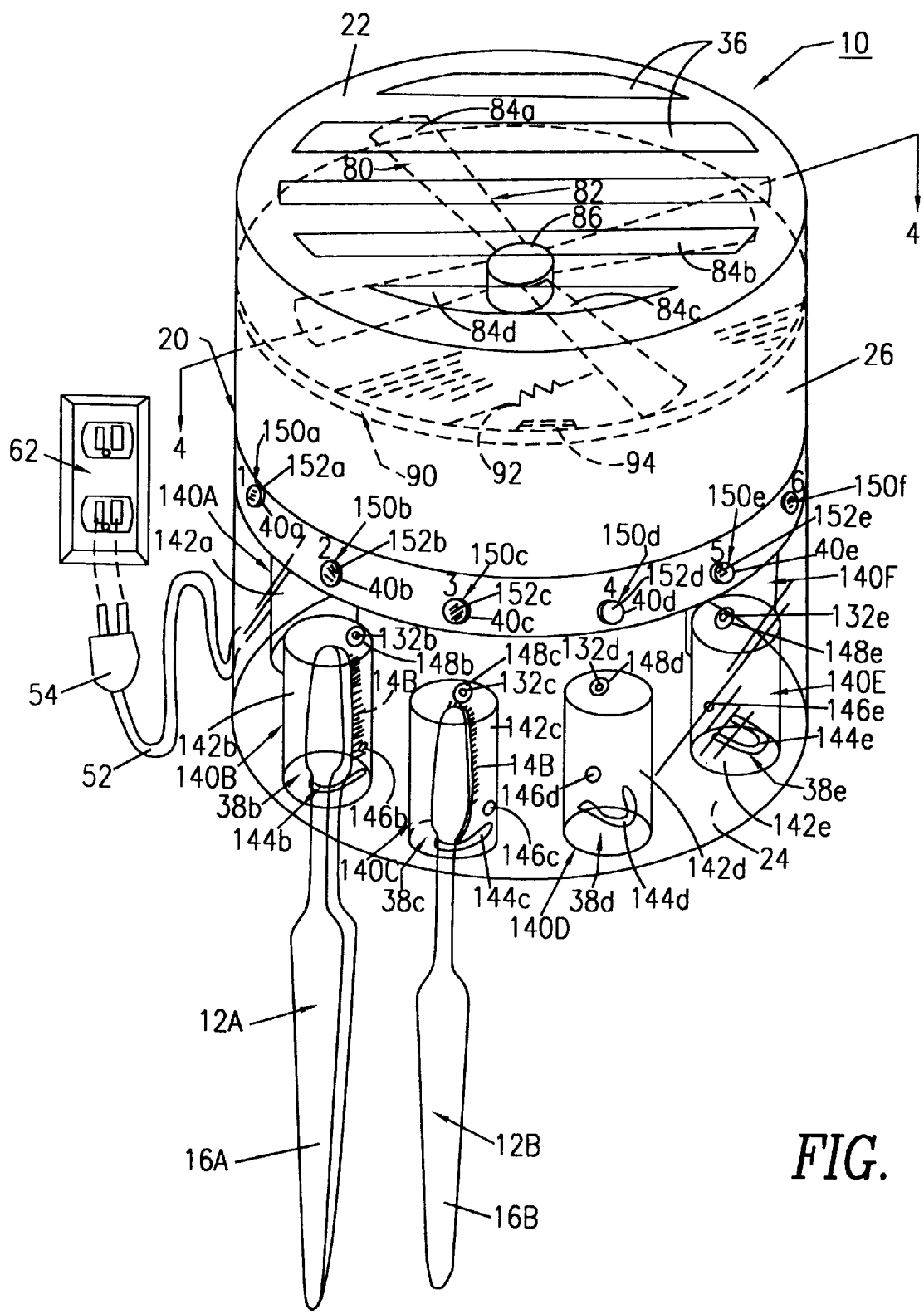
FIG. 1 is a top perspective view of the toothbrush sterilization system of the preferred embodiment of the present invention showing the sterilization device in its assembled state and in operational use.
Figure 2:
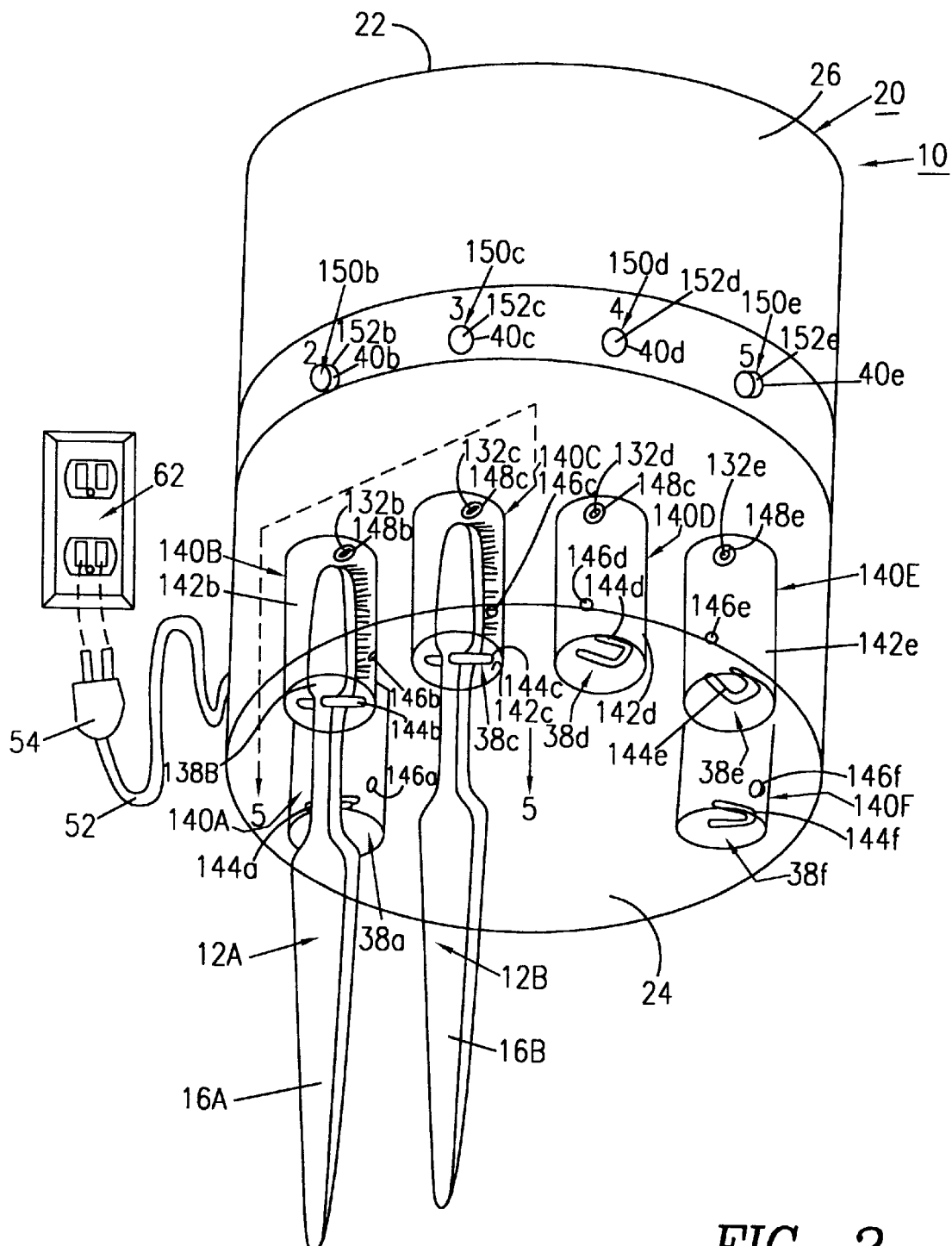
FIG. 2 is a bottom perspective view of the toothbrush sterilization system of the preferred embodiment of the present invention showing the sterilization device in its assembled state and in operational use.
Figure 3:
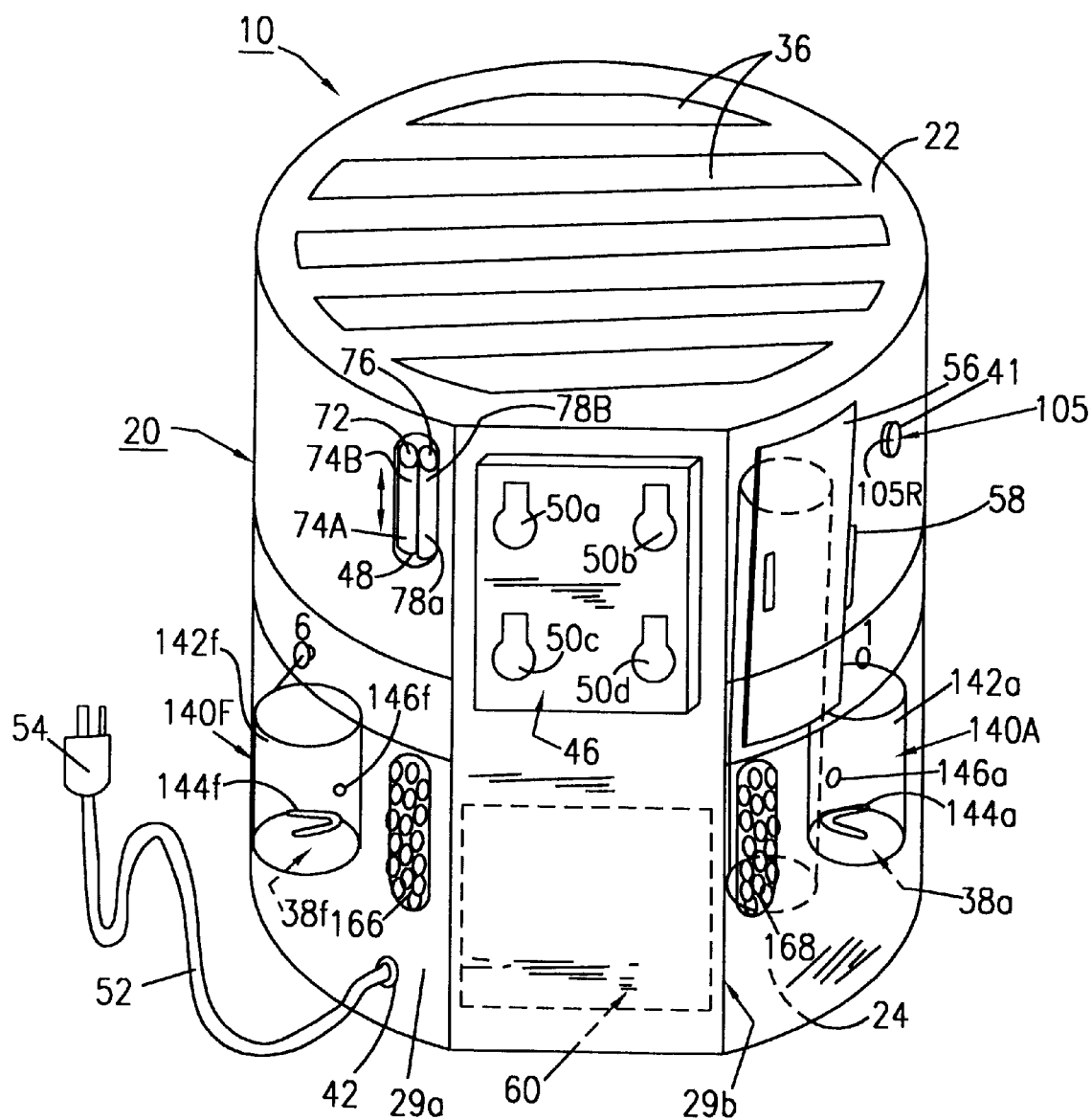
FIG. 3 is a rear perspective view of the toothbrush sterilization system of the present invention showing the wall mounting bracket, the reservoir door for filling the reservoir with disinfectant and the electrical cord and plug for supplying power to the sterilization device.
Figure 4:
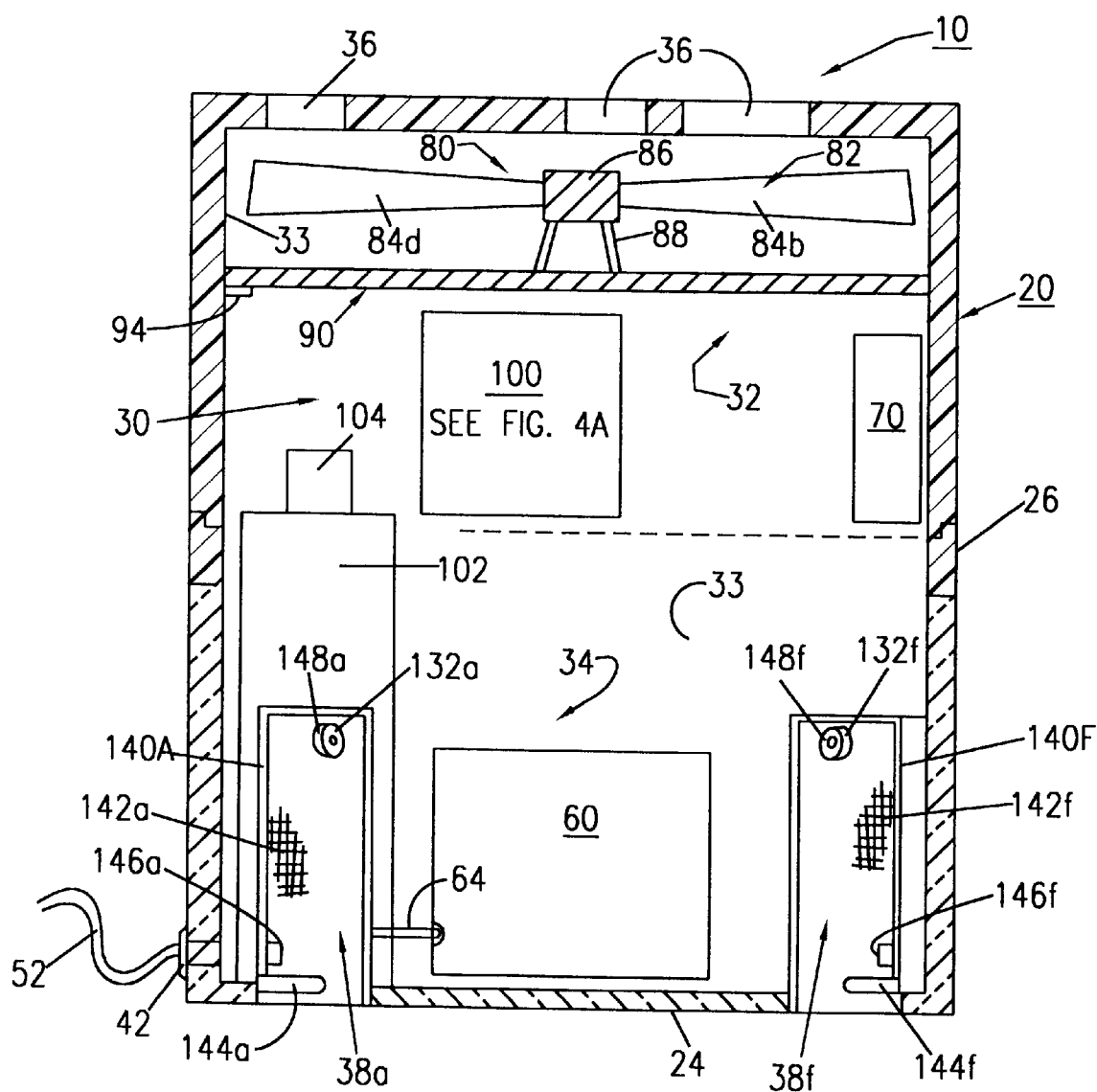
FIG. 4 is a cross-sectional view of the toothbrush sterilization system of the present invention taken along lines 4—4 of FIG. 1 showing the major component parts within the interior compartment of the housing.
Figure 4A:
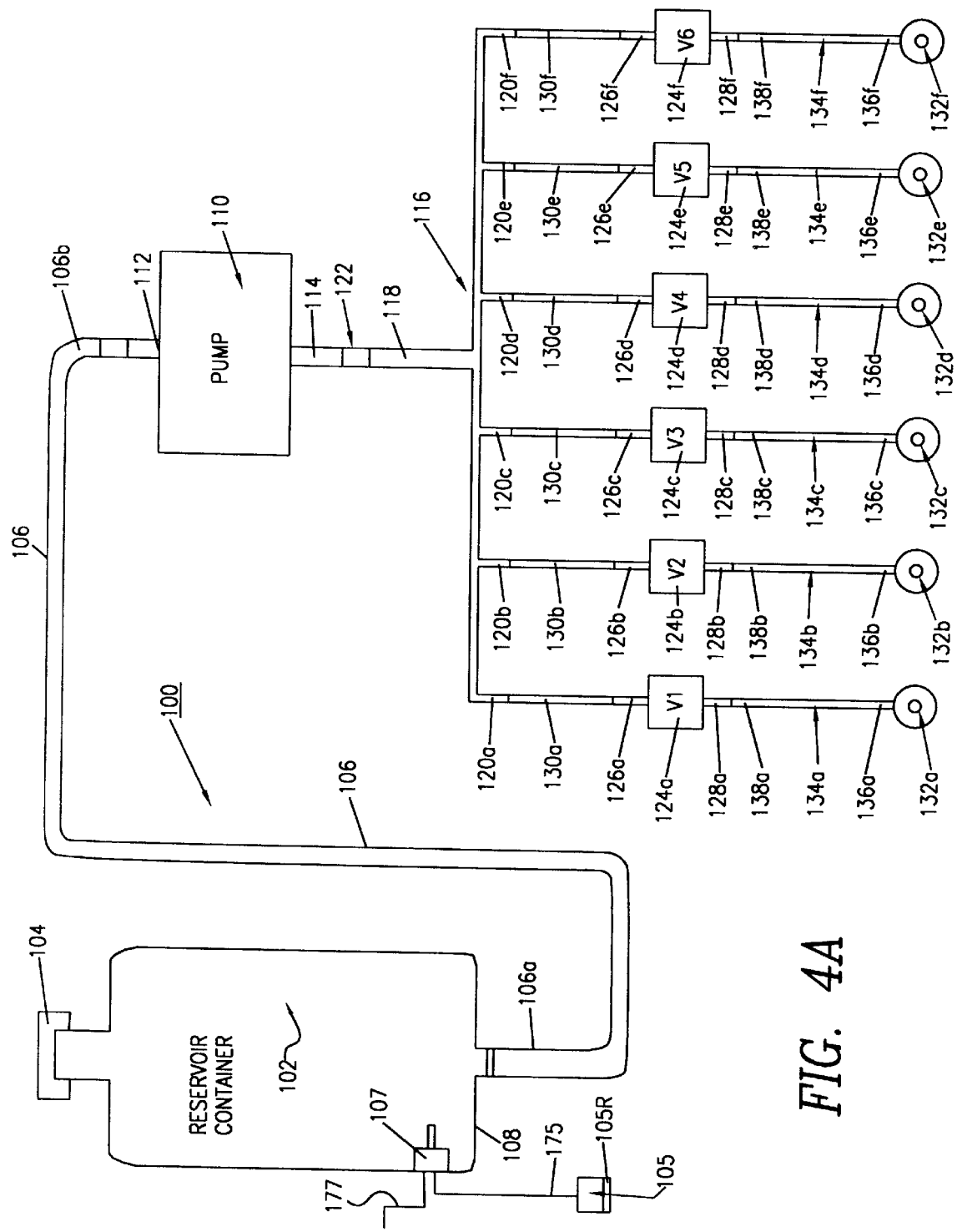
FIG. 4A is a schematic diagram of the toothbrush sterilization system of the present invention showing the pumping system assembly.
Figure 5:
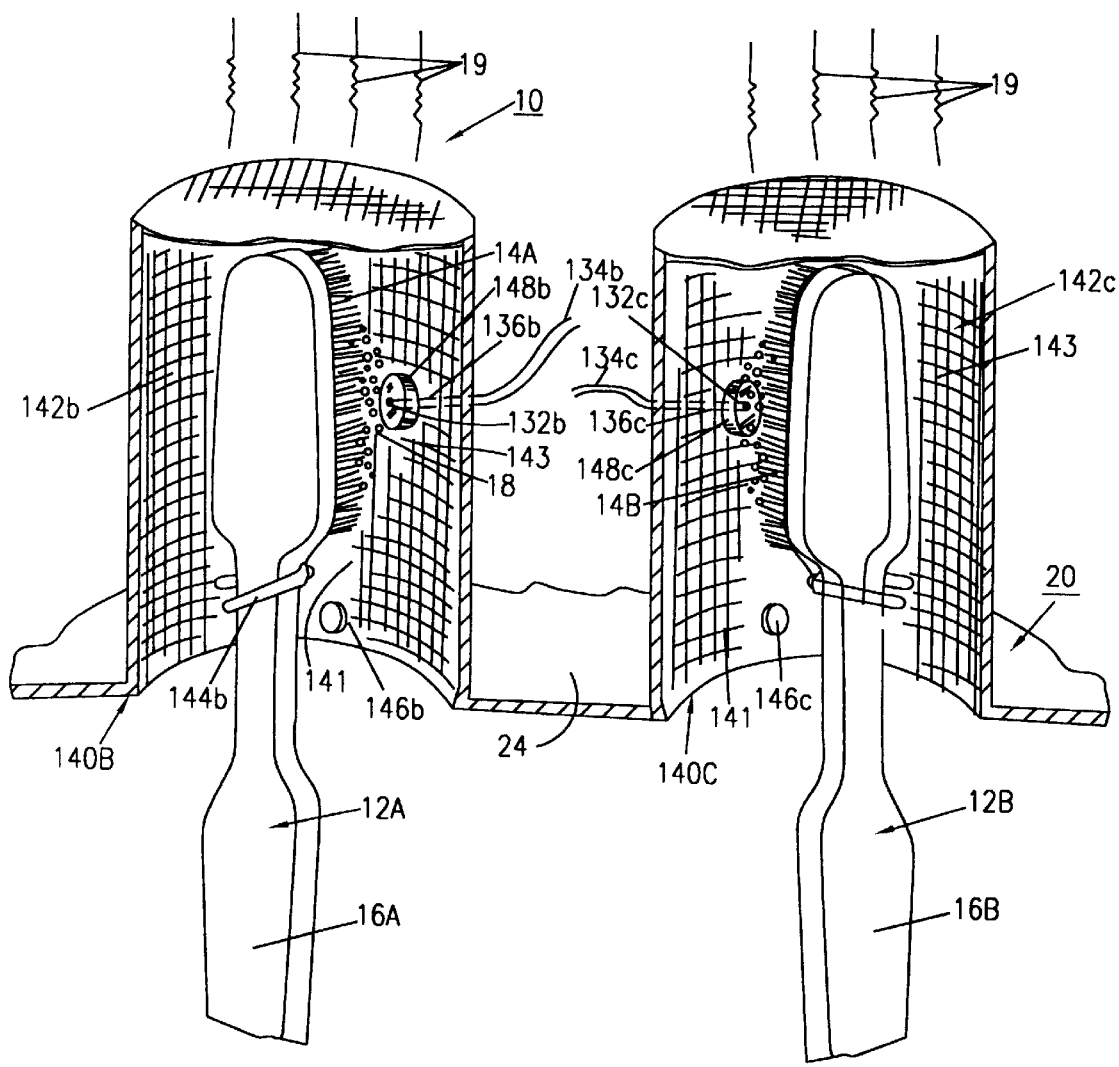
FIG. 5 is a cross-sectional view of the toothbrush sterilization system of the present invention taken along lines 5—5 of FIG. 2 showing the interior well area of the toothbrush docking stations.

The toothbrush sterilization system 10 and its component parts of the preferred embodiment of the present invention are represented in detail by FIGS. 1 through 6 of the patent drawings. The toothbrush sterilization system 10 is used for sterilizing toothbrushes 12 by disinfecting the bristle-head section 14 via the application of an anti-microbial disinfectant liquid spray having droplets or mist 18 to bristles 14 of toothbrush 12, as depicted in FIGS. 1, 2 and 5 of the drawings. The toothbrush sterilization system 10, as shown in FIGS. 2, 4 and 5, includes a sterilization housing 20 being substantially cylindrical in shape, and having a top wall 22, a bottom wall 24, an outer curved wall 26 and a rear wall 28. Housing 20 further includes an interior cavity or compartment 30 having an upper compartment section 32 and a lower compartment section 34. The upper compartment section 32 includes a programmable logic controller (PLC) circuit chip 60 for controlling the dispensing of the disinfectant liquid spray 18 onto the bristle-head 14; a timer mechanism 70 for controlling the length of time for drying the bristle-head 14 of disinfectant liquid 18 via hot air 19, and for controlling the amount of disinfectant liquid spray 18 being dispensed onto the bristle-head 14; a rotary fan 80 having a heating element grid member 90 attached thereto for producing a hot air 19 current or air flow 19 for drying the bristle-head 14 of disinfectant liquid 18; and a pumping system assembly 100 for dispensing of the anti-microbial disinfectant liquid spray 18 onto the bristle-head section 14 of toothbrush 12. The lower compartment section 34 includes a plurality of docking stations 140A to 140F for holding in place the multiple toothbrushes 12. Housing 20 is made from a light-weight, moldable and durable plastic being transparent or colored or combinations thereof or is made from a lightweight, formable and durable metal such as aluminum or stainless steel.

As shown in FIG. 1 of the drawings, top wall 22 includes a plurality of air vent openings 36 for receiving ambient air 19 therethrough. As shown in FIG. 2 of the drawings, bottom wall 24 includes a plurality of oval or circular slot openings 38a, 38b, 38c, 38d, 38e and 38f, each for receiving a single toothbrush 12 within each opening 38a to 38f to be held within each docking station 140A to 140F. As shown in FIGS. 1 to 3 of the drawings, the outer curved wall 26 includes a plurality of circular hole openings 40a, 40b, 40c, 40d, 40e and 40f for receiving indicator lights 150a to 150f, respectively, therein; a circular hole opening 41 for receiving an indicator light 105 therein for indicating when the level of disinfectant liquid 18 is low; an oval hole opening 42 for receiving the electrical cord 52 with plug 54 therethrough; and a rectangular opening 44 for receiving the reservoir compartment door 56 and hinge 58 thereon. As shown in FIG. 3 of the drawings, rear wall 28 includes a mounting bracket 46 being integrally connected thereto; and an oval hole opening 48 for receiving timer switches or knobs 72 and 76 therethrough. Mounting bracket 46 includes a plurality of keyhole openings 50a, 50b, 50c and 50d for mounting the sterilization housing 20 onto the bathroom wall 15 via screws (not shown), as depicted in FIGS. 1 and 2 of the drawings.

Figure 6:
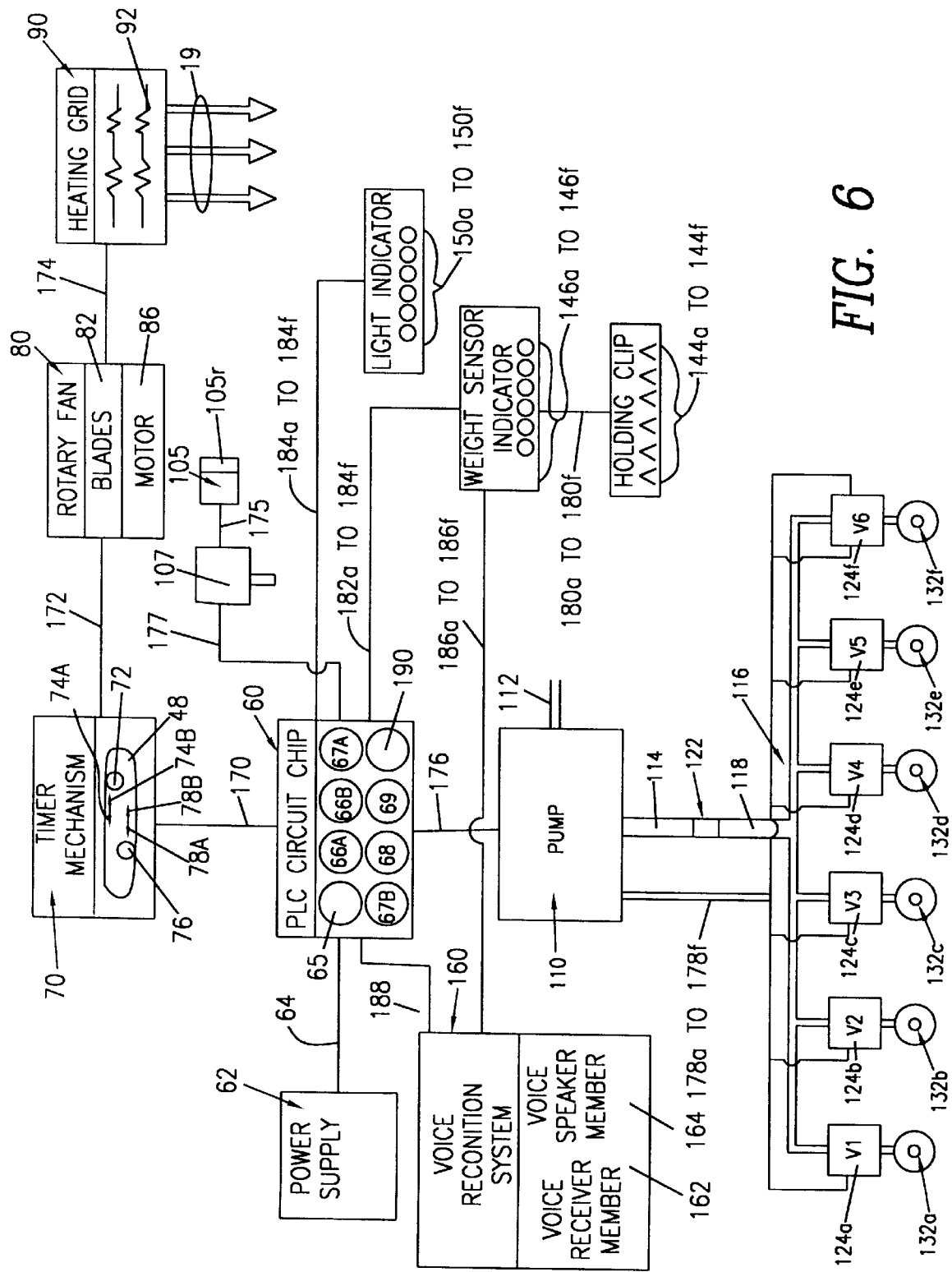
FIG. 6 is an electrical schematic diagram of the toothbrush sterilization system of the present invention showing the electrical circuit for automatically dispensing the anti-microbial disinfectant spray.

The PLC circuit chip 60, as shown in FIGS. 3 and 4 of the drawings, is supplied power for activation by an electrical outlet receptacle 62 via plug 54 and electrical cord 52. Electrical cord and plug 52 and 54 are electrically connected to circuit chip 60 via electrical line 64. PLC circuit chip 60 includes transistor elements 65, 66A, 66B, 67A, 67B, 68 and 69 for controlling the various output functions of the major electrical component parts of the toothbrush sterilization system 10. Transistor element 65 controls the timer mechanism 70; transistor element 66A controls the rotary fan 80; transistor element 66B controls the heating element grid member 90; transistor elements 67A and 67B controls the miniature pump 110 and the miniature valving members 124a to 124f of pumping system assembly 100; transistor element 68 controls the weight sensor indicator members 146a to 146f located within docking stations 140A to 140F; and transistor element 69 controls each of the indicator lights 150a to 150f located on the outer curved wall 26, as shown in FIG. 6 of the drawings.

Timer mechanism 70 includes a first timer switch or knob 72 having switch positions or knob positions 74A or 74B for increasing or decreasing the length of time that rotary fan motor 86 is in the "ON" mode as well as the length of time the miniature pump 110 is in the "ON" mode. Timer mechanism 70 further includes a second switch or knob 76 having switch or knob positions 78A and 78B for indicating the length of time that may be changed for either the rotary fan motor 86 or the miniature pump 110. Timer mechanism 70 is connected to the interior wall surface 33 of the upper compartment section 32, and is adjacent to the rear wall 28, as shown in FIGS. 3 and 4 of the drawings. Timer mechanism 70 is electrically connected to the PLC circuit chip 60 via electrical line 170, as shown in FIG. 6 of the drawings. Optionally, the timer mechanism 70 can include preset time durations for a specific length of time for controlling the rotary fan 80 and the heating element grid member 90, as well as for controlling the miniature pump 110 for dispensing the disinfectant liquid 18. With this option, first and second switches or knobs 72 and 76 within timer mechanism 70 are not necessary.

Rotary fan 80, as depicted in FIG. 4 of the drawings, includes a rotary blade member 82 having four (4) blades 84a to 84d for moving the ambient air 19 downwardly, and an electrical rotary fan motor 86 for rotating the rotary blade member 82 in a circular movement. Rotary fan 80 also includes a fan bracket 88 being connected to the interior wall surface 33 of the upper compartment section 32. Rotary fan 80 is electrically connected to the timer mechanism 70 via electrical line 172, as shown in FIG. 6 of the drawings.

Heating element grid member 90, as shown in FIG. 4 of the drawings, includes a plurality of electrical heating elements 92 supported on a grid and frame bracket 94. Bracket 94 is attached to the interior wall surface 33 of the upper compartment section 32. Heating elements 92 heat-up the ambient air 19 from rotary fan 80 to hot air 19 in order to dry off the disinfectant liquid spray 18 from the bristle section 14 of toothbrush 12. Heating element grid member 90 is electrically connected to the rotary fan 80 via electrical line 174, as shown in FIG. 6 of the drawings.

Pumping system assembly 100, as shown in FIGS. 4, 5 and 6 of the drawings, includes a disinfectant reservoir container 102 having a snap-on cap 104, a discharge tube 106 being connected at one end 106a to the bottom wall 108 of container 102; and a miniature pump 110 having an inlet port 112 connected to the other end 106b of discharge tube 106, and having an outlet port 114 connected to a discharge manifold transfer member 116. Pumping system assembly 100, also includes an indicator light 105 for indicating a low level of disinfectant liquid 18 in reservoir container 102. Indicator light 105 is electrically connected to a liquid level transmitter 107 via electrical line 175, and liquid level transmitter is connected to the PLC circuit chip 60 via electrical line 177. Indicator light 105 has a red lens cover 105R and is adjacent to the reservoir compartment door 56, as shown in FIG. 3 of the drawings. Manifold transfer member 116 includes one manifold inlet port 118 and six (6) manifold discharge outlet ports 120a to 120f. Outlet port 114 of miniature pump 110 is connected to manifold inlet port 118 via connecting coupler 122. Pumping system assembly 100 further includes a plurality of electronically controlled valves 124a to 124f having inlet and outlet shunts 126a to 126f and 128a to 128f, respectively. Each of the discharge ports 120a to 120f of manifold 116 are connected to the inlet shunts 126a to 126f of valves 124a to 124f, respectively, via connecting tubes 130a to 130f, respectively. Additionally, pumping system assembly 100 also includes a plurality of atomizer nozzles 132a to 132f for applying a fine mist spray of anti-microbial disinfectant liquid 18 to the bristle-head 14 of each toothbrush 12 within docking stations 140A to 140F. The atomizer nozzles 132a to 132f are connected to a plurality of discharge tubes 134a to 134f at one end 136a to 136f and connected at the other end 138a to 138f to each of the outlet shunts 128a to 128f of valves 124a to 124f, respectively. Miniature pump 110 is electrically connected to the PLC circuit chip 60 via electrical line 176; and each of the miniature valves 124a to 124f are connected to the PLC circuit chip 60 via electrical lines 178a to 178f, as depicted in FIG. 6 of the drawings.

Each docking station 140A to 140F, as shown in FIGS. 1, 2 and 5 of the drawings, includes a cavity-type housing 142a to 142f being made from a porous plastic material or a wire-mesh material in order to permit the hot air 19 to flow through each cavity-type housing 142a to 142f for drying the disinfectant spray liquid 18 on each toothbrush 12. Each cavity-type housing 142a to 142f is connected to each slot opening 38a to 38f, respectively, on the bottom wall 24 by means of gluing, welding, laser bonding or the like. Each docking station 140A to 140F further includes a toothbrush holding clip 144a to 144f electronically attached to a weight sensor indicator 146a to 146f for indicating when a toothbrush 12 or a detachable toothbrush head of an electric toothbrush (not shown) has been placed within a holding clip 144a to 144f. The weight sensor indicator 146a to 146f then signals the PLC circuit chip 60 to initiate the pumping of the disinfectant liquid 18 by miniature pump 110 onto the bristle head 14 of toothbrush 12 for a specific period of time, as well as starting-up the rotary fan 80 and heating element grid member 90 in order to blow hot air 19 through the cavity type housings 142a to 142f for drying of the disinfectant spray liquid 18 on the bristle section 14 of the toothbrush 12 for a specific period of time. Each holding clip 144a to 144f and each weight sensor indicator 146a to 146f is attached at the lower end 141 of each cavity-type housing 142a to 142f, as shown in FIG. 5 of the drawings. Docking stations 140A to 140F also include centrally located hole openings 148a to 148f positioned near the upper end 143 of each cavity-type housing 142a to 142f for receiving each of the atomizer nozzles 132a to 132f therethrough, respectively. Additionally, docking stations 140A to 140F, as depicted in FIGS. 1, 2, 4 and 6, include indicator lights 150a to 150f having a green lens cover 152a to 152f thereon received within circular hole openings 40a to 40f, respectively, on outer curved wall 26. Indicator lights 150a to 150f are used to indicate when each toothbrush 12 is dry from the disinfectant liquid spray 18 and is ready for reuse by lighting-up "green" for the user. Indicator lights 150a to 150f are in the form of miniature light bulbs, LEDs or fiber optic elements. Lens covers 152a to 152f can have other colors such as yellow, amber, red, blue, orange or white. Each holding clip 144a to 144f is electrically connected to each weight sensor indicator 146a to 146f via electrical lines 180a to 180f and each weight sensor indicator 146a to 146f is electrically connected to the PLC circuit chip 60 via electrical lines 182a to 182f. Each indicator light 150a to 150f is electrically connected to the PLC circuit chip 60 via electrical lines 184a to 184f.

Additionally, the toothbrush sterilization system 10 further includes a voice recognition system 160 in conjunction with each of the indicator lights 150a to 150f to tell each user which toothbrush 12 is theirs when any given toothbrush 12 is removed from its personal docking station 140A to 140F by the flashing "green" of one of the indicator lights 150a to 150f, as shown in FIGS. 3, 4 and 6 of the drawings. The voice recognition system 160 includes a voice receiver member 162 for transmitting incoming voice commands and a voice speaker member 164 for transferring of voice protocols to the user for indicating which toothbrush is theirs for a particular docking station 140A to 140F. The voice receiver member 162 is attached to a first oval perforated hole opening area 166 on outer curved wall 26 adjacent to one side 29a of rear wall 28, as shown in FIG. 3. The voice speaker member 164 is attached to a second oval perforated hole opening area 168 on outer curved wall 26 adjacent to the other side 29b of rear wall 28, as shown in FIG. 3. The voice recognition system 160 is electronically connected to each of the indicator lights 50a to 150f via electrical lines 186a to 186f.

Detailed Description of the Alternate Embodiment
200

Figure 7:
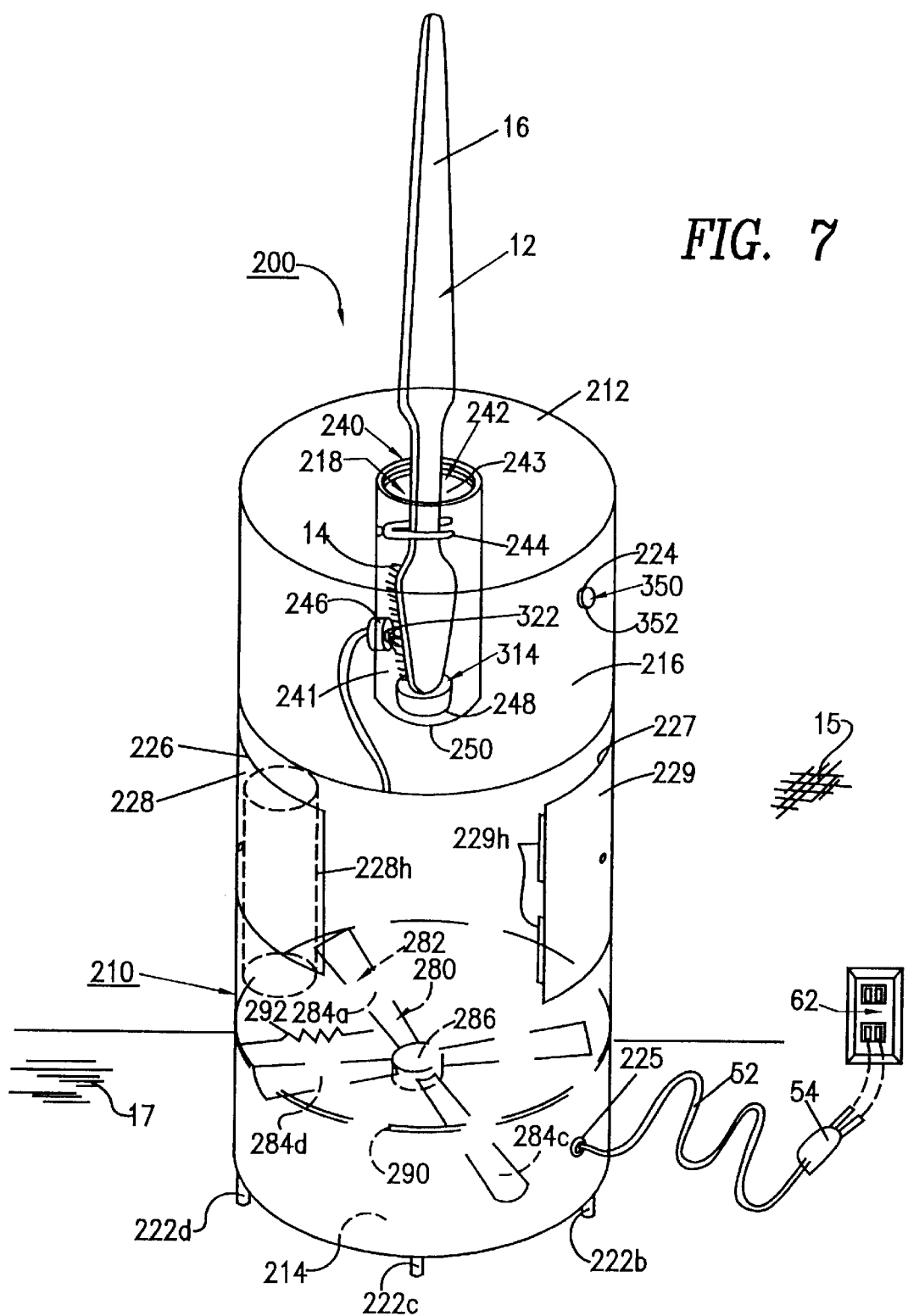
FIG. 7 is a top rear perspective view of the toothbrush sterilization system of the first alternate embodiment of the present invention showing the sterilization device in its assembled stated and in operational use.
Figure 8:
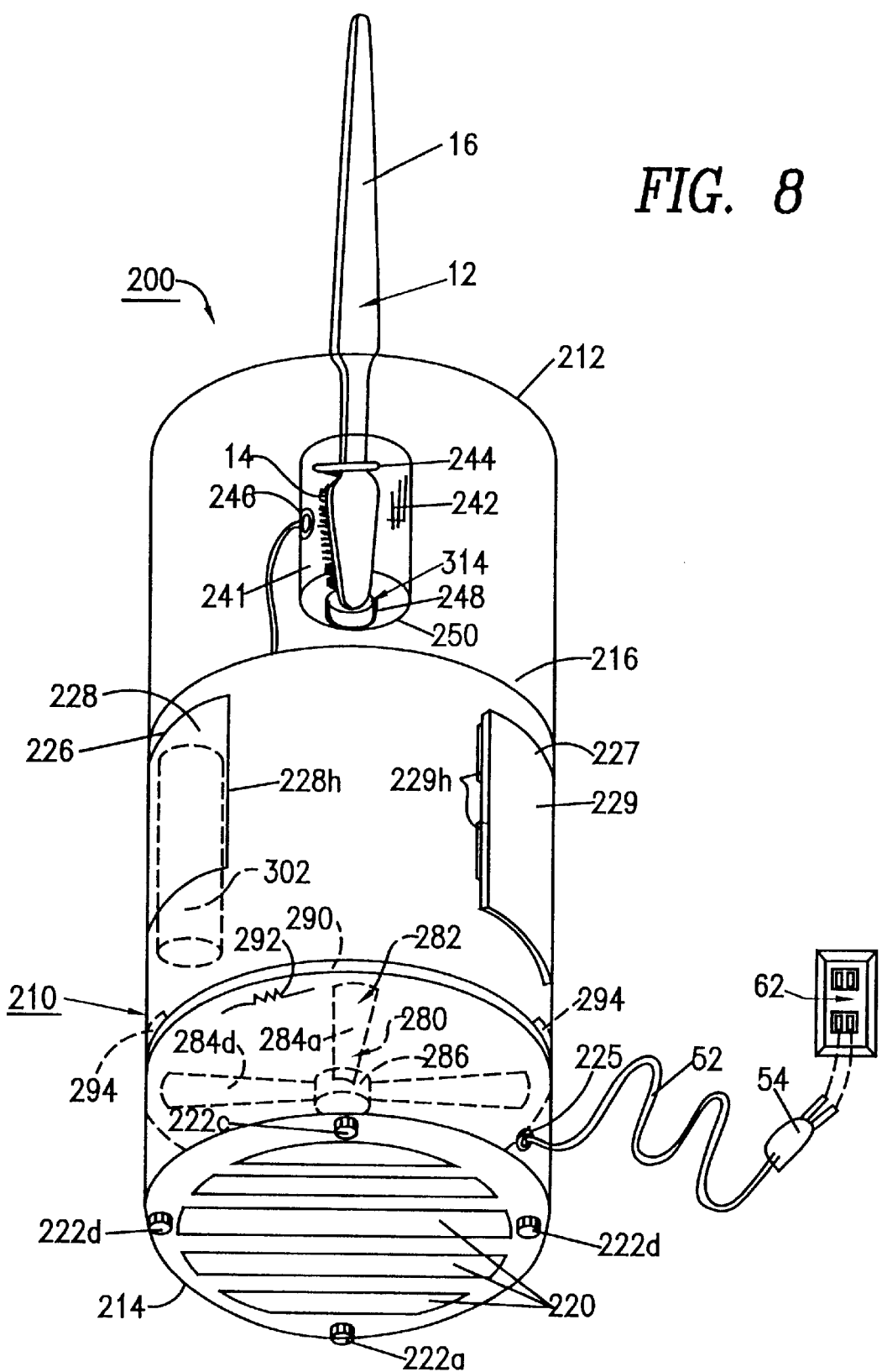
FIG. 8 is a bottom perspective view of the toothbrush sterilization system of the first alternate embodiment of the present invention showing the sterilization device in its assembled stated and in operational use.
Figure 9:
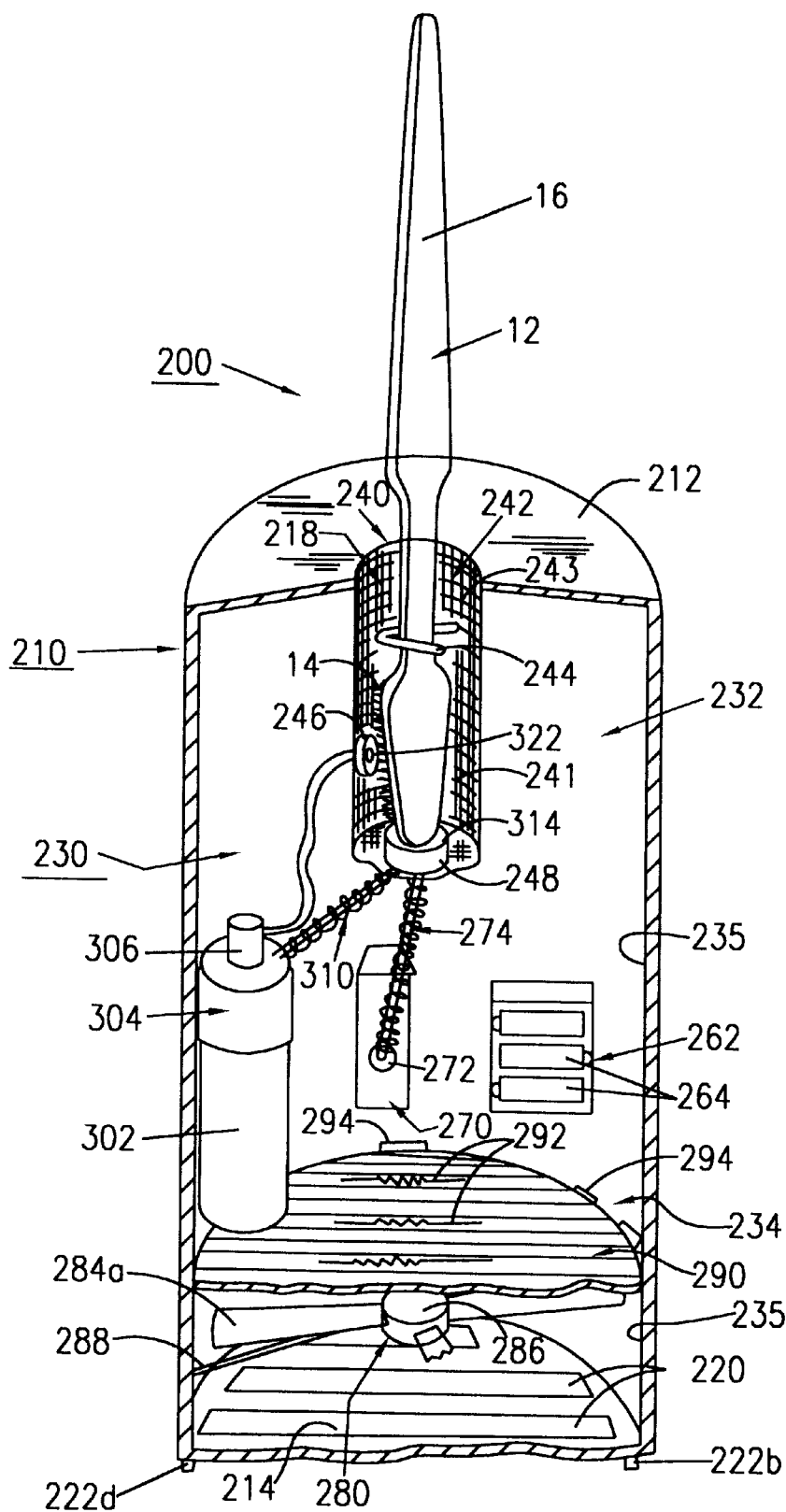
FIG. 9 is a cross-sectional view of the toothbrush sterilization system of the present invention taken along lines 9—9 of FIG. 7 showing the major component parts within the interior compartment of the housing.
Figure 10:
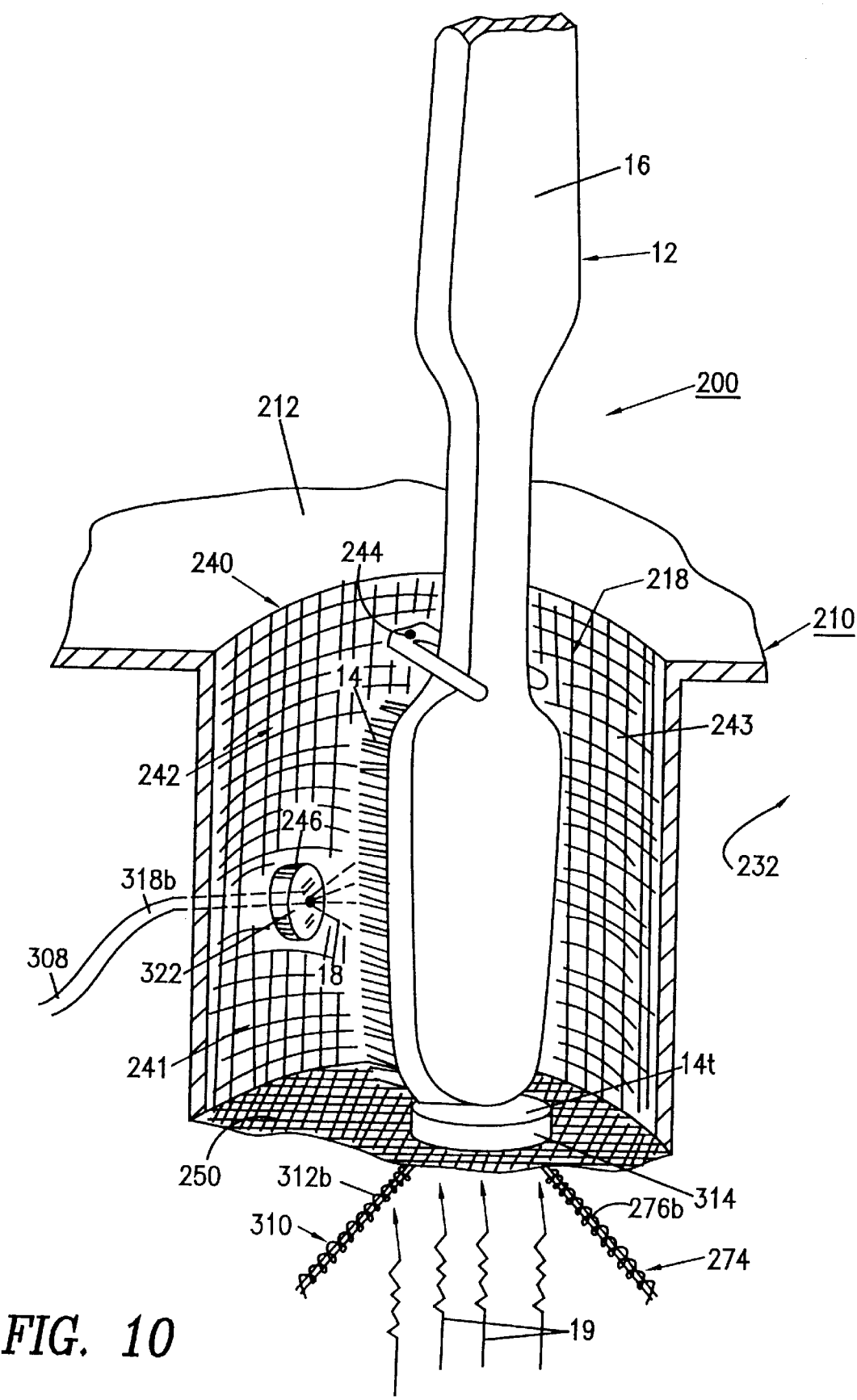
FIG. 10 is a cross-sectional view of the toothbrush sterilization system of the present invention taken along lines 10—10 of FIG. 8 showing the interior well area of an individual docking station.

The toothbrush sterilization system 200 and its component parts of the first alternate embodiment of the present invention are represented in detail by FIGS. 7 through 11 of the patent drawings. The toothbrush sterilization system 200 is used for sterilizing a single toothbrush 12 by disinfecting the bristle-head section 14 via the manual application of an anti-microbial disinfectant liquid spray mist 18 to the bristles 14 of toothbrush 12, as depicted in FIGS. 7, 8, 10 and 11 of the drawings. The toothbrush sterilization system 200, as shown in FIGS. 7 and 10, includes a sterilization housing 210 being cylindrical in shape, and having a top wall 212, a bottom wall 214 and an outer curved wall 216. Housing 210 further includes an interior compartment 230 having an upper compartment section 232 and a lower compartment section 234. The upper compartment section 232 includes a single docking station 240 for holding a single toothbrush 12 in place. The lower compartment section 234 includes a power source 260A in the form of a battery compartment 262 having a plurality of "AA" batteries 264 therein for portability; or power source 260B can be in the form of an electrical outlet receptacle 62 via plug 54 and electrical cord 52. Electrical cord and plug 52 and 54 are connected to a by-pass switch 266 from by-pass junction box 268J via electrical line 268 for by-passing battery compartment 262 when using the outlet receptacle 62. Battery compartment 262 is connected to the by-pass switch 266 from by-pass junction box 268J via electrical line 269 when using batteries 264 when sterilization unit 200 is in a portable mode. The lower compartment section 234 further includes a timer mechanism 270 for controlling the length of time for drying the bristle-head 14 of disinfectant liquid spray 18 via hot air 19; a rotary fan 280 having a heating element grid member 290 attached thereto for producing a hot air current or air flow 19 for drying of the bristle-head 14 of disinfectant liquid 18; and a pumping system assembly 300 for dispensing of the anti-microbial disinfectant liquid spray 18 onto the bristle-head section 14 of a single toothbrush 12. Housing 210 is made from a light-weight and durable plastic being transparent or colored or combinations thereof; or is made from a light-weight and durable metal such as aluminum or stainless steel.

As shown in FIG. 7 of the drawings, top wall 212 includes an oval opening 218 for receiving a single toothbrush 12 within docking station 240. As shown in FIG. 8 of the drawings, bottom wall 214 includes a plurality of air vent openings 220 for receiving of ambient air 19 therethrough, and a plurality of rubber foot pads 222a to 222d for standing the housing 210 in a vertical position on a horizontal counter top 17 such as bathroom sink. As shown in FIGS. 7 and 8 of the drawings, the outer curved wall 216 includes a circular hole opening 224 for receiving an indicator light 350 therein; and an oval hole opening 225 for receiving the electrical cord 52 with plug 54 therethrough; and a first rectangular opening 226 for receiving the reservoir compartment door 228 and hinge 228h thereon. Outer curved wall 216 also includes a second rectangular opening 227 for receiving the battery compartment door 229 and hinge 229h thereon.

Docking station 240, as shown in FIGS. 7 and 10 of the drawings, includes a cavity-type (well) housing 242 made from a porous plastic material or a wire-mesh material in order to permit the hot air 19 to flow through cavity-type housing 242 for drying of the disinfectant spray liquid 18 on the bristle-head 14 of toothbrush 12. Cavity-type housing 242 is connected to oval opening 218 on top wall 212 by means of gluing, welding, laser bonding and the like. Docking station 240 further includes a toothbrush holding clip 244 for holding the toothbrush 12 in an upright position, as shown in FIGS. 7 and 10 of the drawings; and a centrally located circular hole opening 246 positioned near the lower end 241 of the cavity-type housing 242 for receiving an atomizer nozzle 322 therethrough. Docking station 240 also includes a centrally located circular hole opening 248 positioned on the bottom wall 250 of cavity-type housing 242 for receiving the start-up pump button 314 therethrough. Additionally, docking station 240, as depicted in FIGS. 7 and 8, includes an indicator light 350 having a green lens cover 352 thereon received within circular hole opening 224, respectively, on outer curved wall 216 of housing 210. Indicator light 350 is used to indicate when the single toothbrush 12 is dry from the disinfectant liquid spray 18 and is ready for reuse by lighting-up "green" for the user. Indicator light 350 is in the form of a miniature light bulb, an LED or a fiber optic element. Lens cover 352 can have other colors such as yellow, amber, red, blue, orange or white. Holding clip 244 is attached to the upper end 243 of cavity-type housing 242, as shown in FIG. 10 of the drawings. Holding clip 244 is made of durable and light-weight plastic or metal. Indicator light 350 is electrically connected to the timer mechanism 270 via electrical line 354.

Timer mechanism 270 includes a timer button 272 having a coil-spring attachment member 274 connected to the timer button 272 at one end 276a of the first spring attachment member 274 for initiating the timing sequence (a specific length of time) for the rotary fan 280 and heating element grid member 290 to be in the "ON" mode. Timer mechanism 270 is connected to the interior wall surface 235 of the lower compartment section 234, as shown in FIG. 9 of the drawings. Timer mechanism 270 is electrically connected to the by-pass function box 268J via electrical line 278. The other end 276b of spring attachment member 274 is connected to the initiating and start-up pump button 314 within the single docking station 240, as shown in FIG. 10 of the drawings.

Rotary fan 280, as depicted in FIG. 9 of the drawings, includes a rotary blade member 282 having four (4) blades 284a to 284d for moving the ambient air 19 upwardly, and an electrical rotary fan motor 286 for rotating the rotary blade member 282 in a circular movement. Rotary fan 280 also includes a fan bracket 288 connected to the interior wall surface 235 of the lower compartment section 234. Rotary fan 280 is electrically connected to the timer mechanism 270 via electrical line 289, as shown in FIG. 11 of the drawings.

Heating element grid member 290, as shown in FIG. 9 of the drawings, includes a plurality of electrical heating elements 292 supported on a grid and frame bracket 294. Bracket 294 is attached to the interior wall surface 235 of the lower compartment section 234. Heating elements 292 heat-up the ambient air 19 from rotary fan 280 to hot air 19 in order to dry off the disinfectant liquid spray 18 from the bristle-head section 14 of toothbrush 12. Heating element grid member 290 is electrically connected to the rotary fan 280 via electrical line 298, as shown in FIG. 11 of the drawings.

Figure 11:
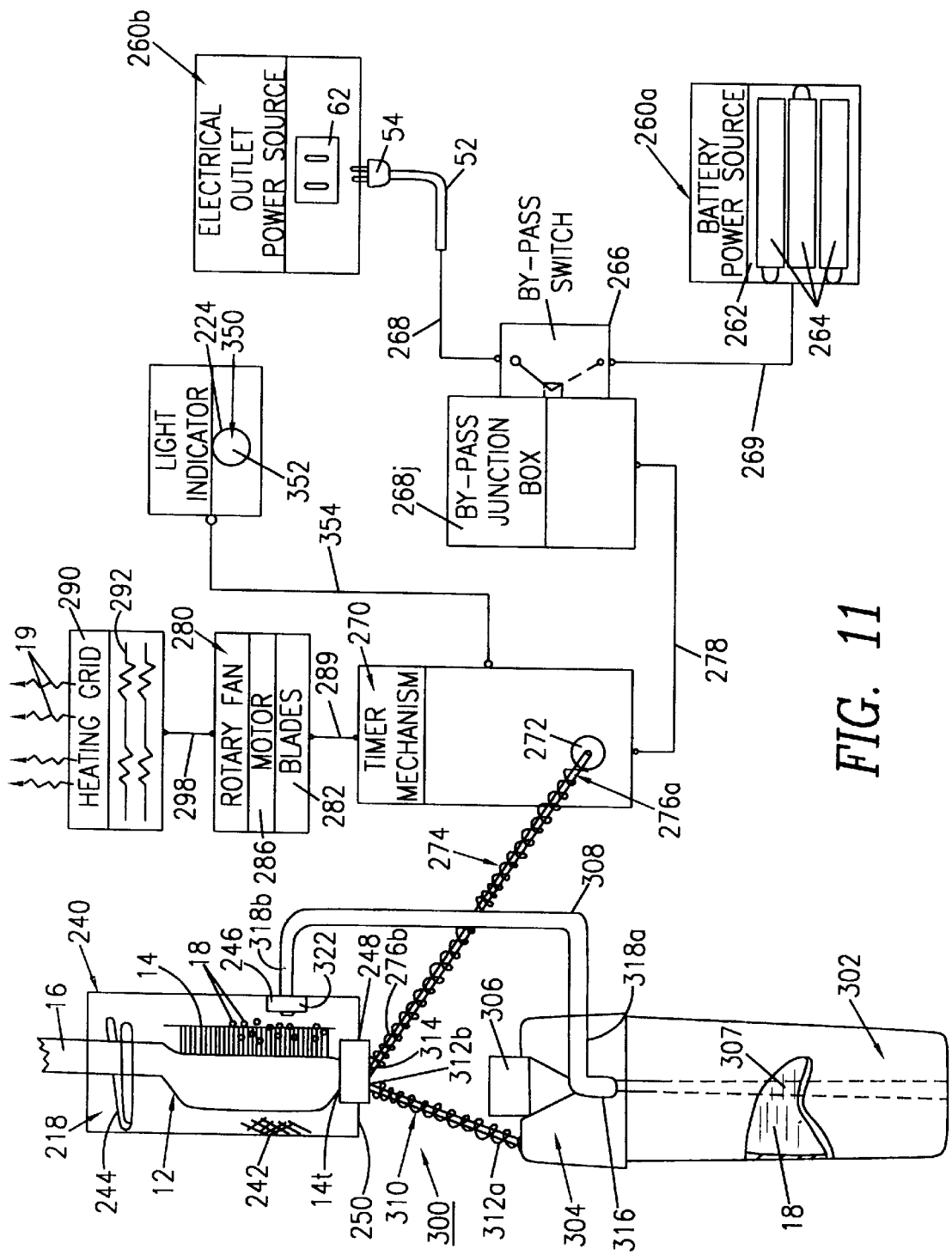
FIG. 11 is a pumping system and an electrical schematic diagram of the toothbrush sterilization system of the present invention showing the pumping system for dispersing the disinfectant liquid and the electrical circuit for notifying the user that the toothbrush has been sterilized.

Pumping system assembly 300, as depicted in FIGS. 9 and 11 of the drawings, includes a disinfectant reservoir container 302 having a pump head member 304 with a removable screw-on cap 306. Pump head member 304 includes an intake tube 307 and a discharge tube 308 being connected to the pump head member 304. Pump head member 304 further includes a second coil-spring attachment member 310 attached at one end 312a to the pump head member 304. The other end 312b of spring attachment member 310 is connected to the start-up pump button 314 within the single docking station 340, as shown in FIGS. 9 and 10 of the drawings. Pump head member 304 also includes a centrally located circular hole opening 316 for receiving at one end 318a the discharge tube 308; and at the other end 318b of discharge tube 308 there is an atomizer nozzle 322 connected thereto. Atomizer nozzle 322 is received within circular hole opening 246 for the discharging of the disinfectant spray liquid 18 onto the bristle-head section 14 of toothbrush 12, as shown in FIG. 10.

Second Alternate Embodiment 400

Figure 12:
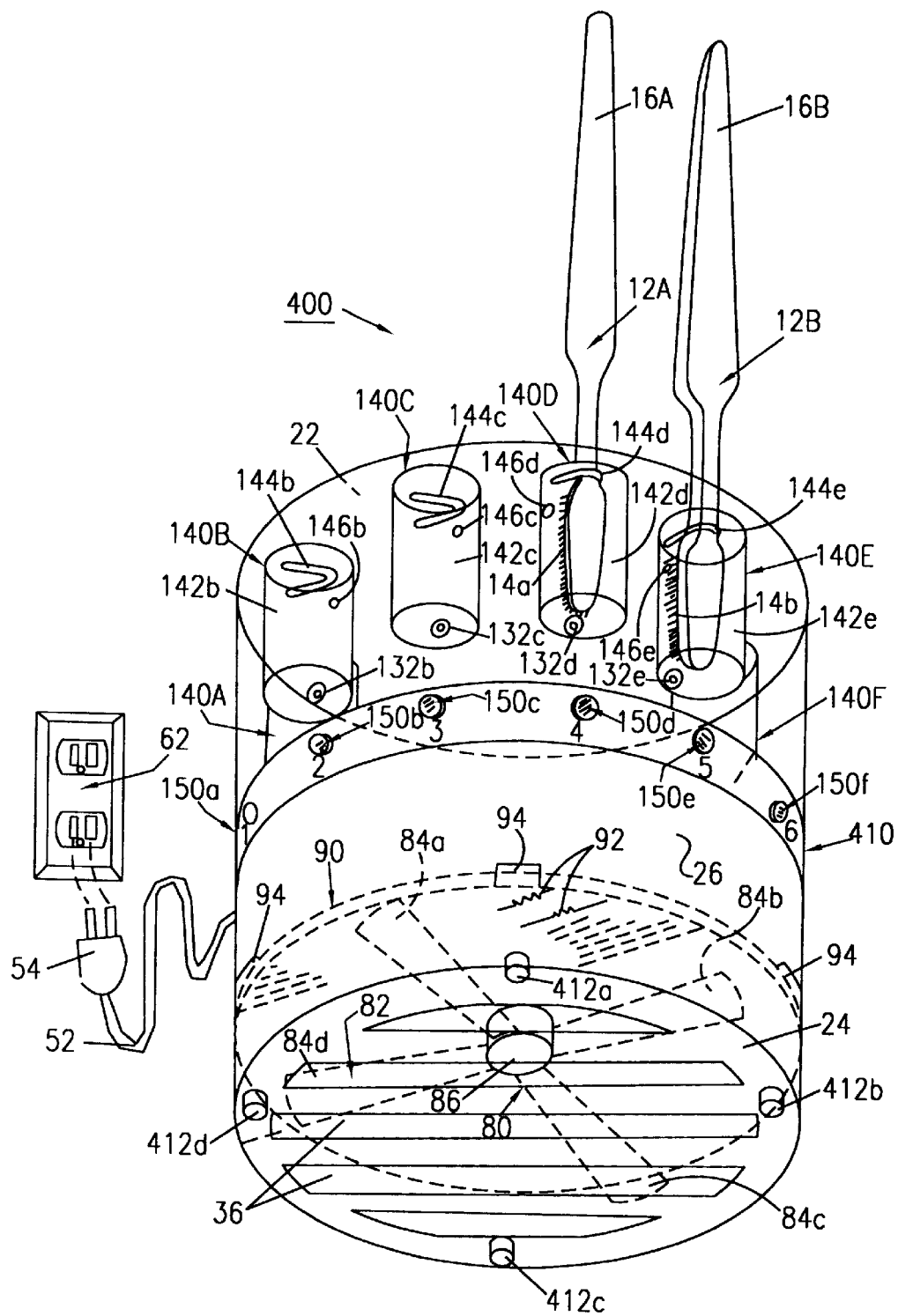
FIG. 12 is a top perspective view of the toothbrush sterilization system of the second alternate embodiment of the present invention showing the sterilization device in its assembled state and in operational use.
Figure 13:
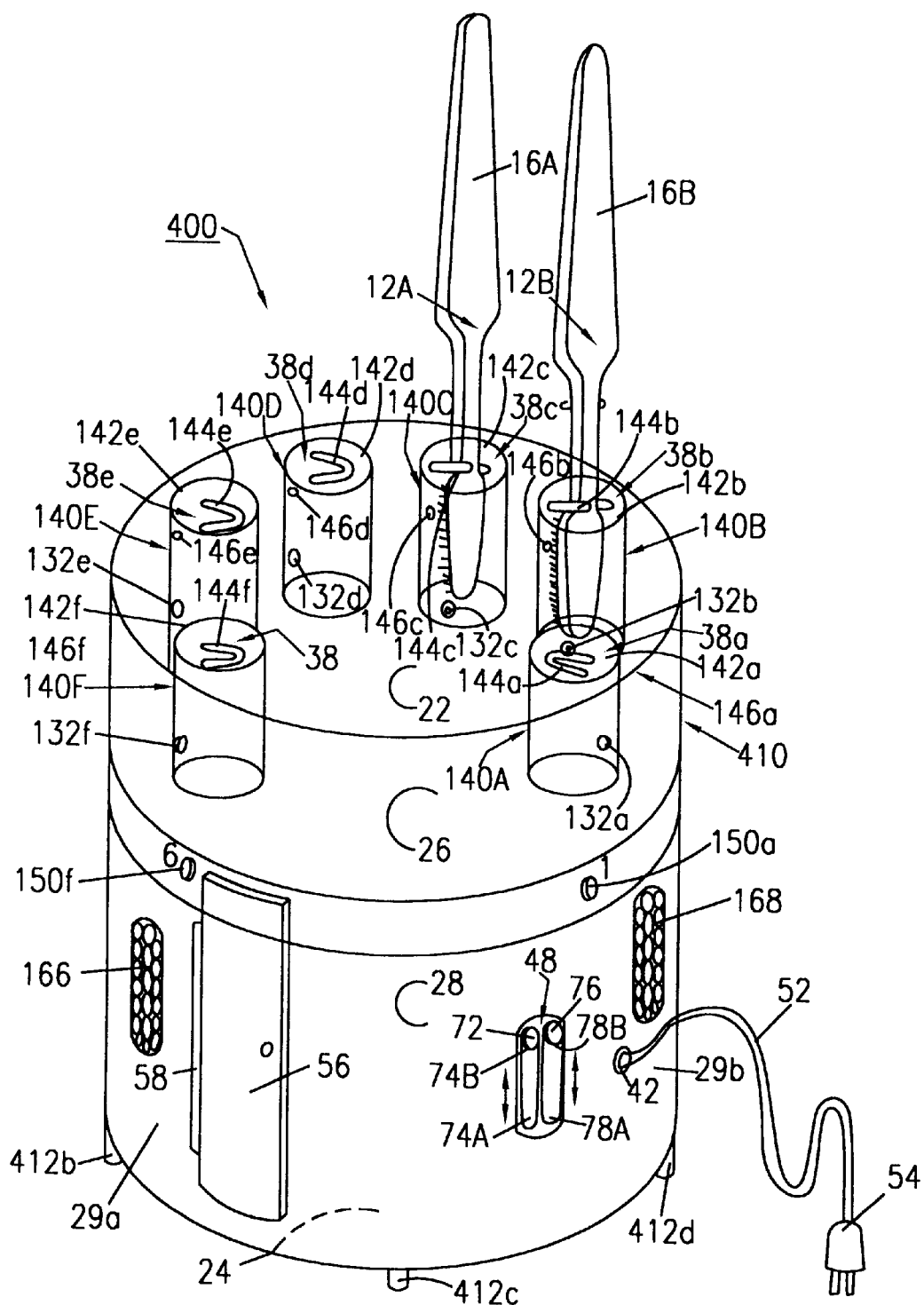
FIG. 13 is a rear perspective view of the toothbrush sterilization system of the second alternate embodiment of the present invention showing the docking stations, the reservoir door for filling the reservoir with disinfectant, and the electrical cord and plug for supplying power to the sterilization device.

The toothbrush sterilization system 400 and its component parts of the second alternate embodiment are represented in detail by FIGS. 12 and 13 of the patent drawings. All aspects of the second alternate embodiment of the toothbrush sterilization system 400 are the same as the preferred embodiment of the toothbrush sterilization system 410, except for the shape of the sterilization housing 410. There is no rear wall 28 having the mounting bracket 46 thereon. The bottom wall 24 has a plurality of foot-pad members 412a to 412d thereon for standing the housing 410 in a vertical position on a horizontal counter top 17, such as a bathroom sink. Preferably, housing 410 is substantially cylindrical in shape, but can have other shapes.

Third Alternate Embodiment 500

Figure 14:
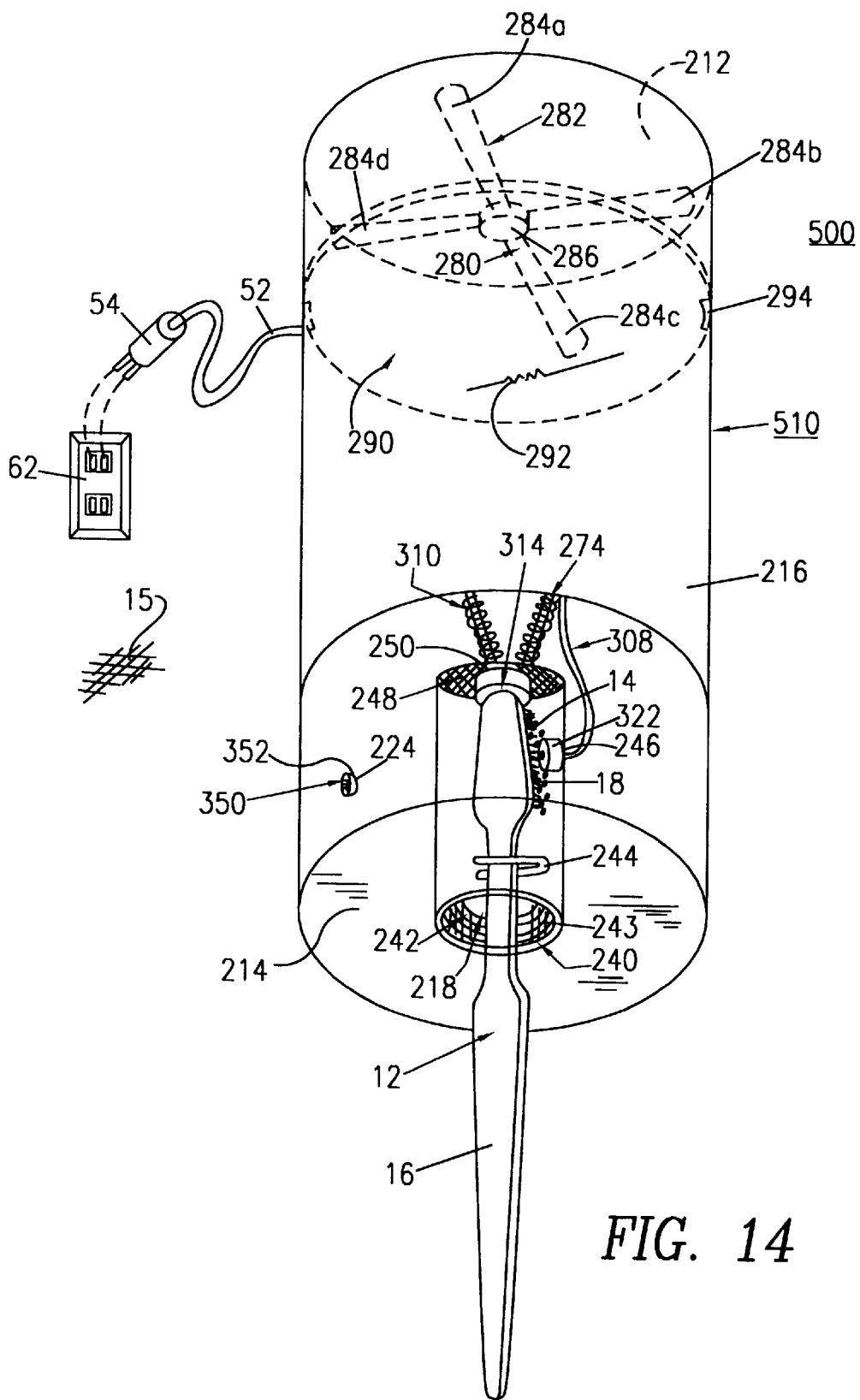
FIG. 14 is a top perspective view of the toothbrush sterilization system of the third alternate embodiment of the present invention showing the sterilization device in its assembled state and in operational use.
Figure 15:
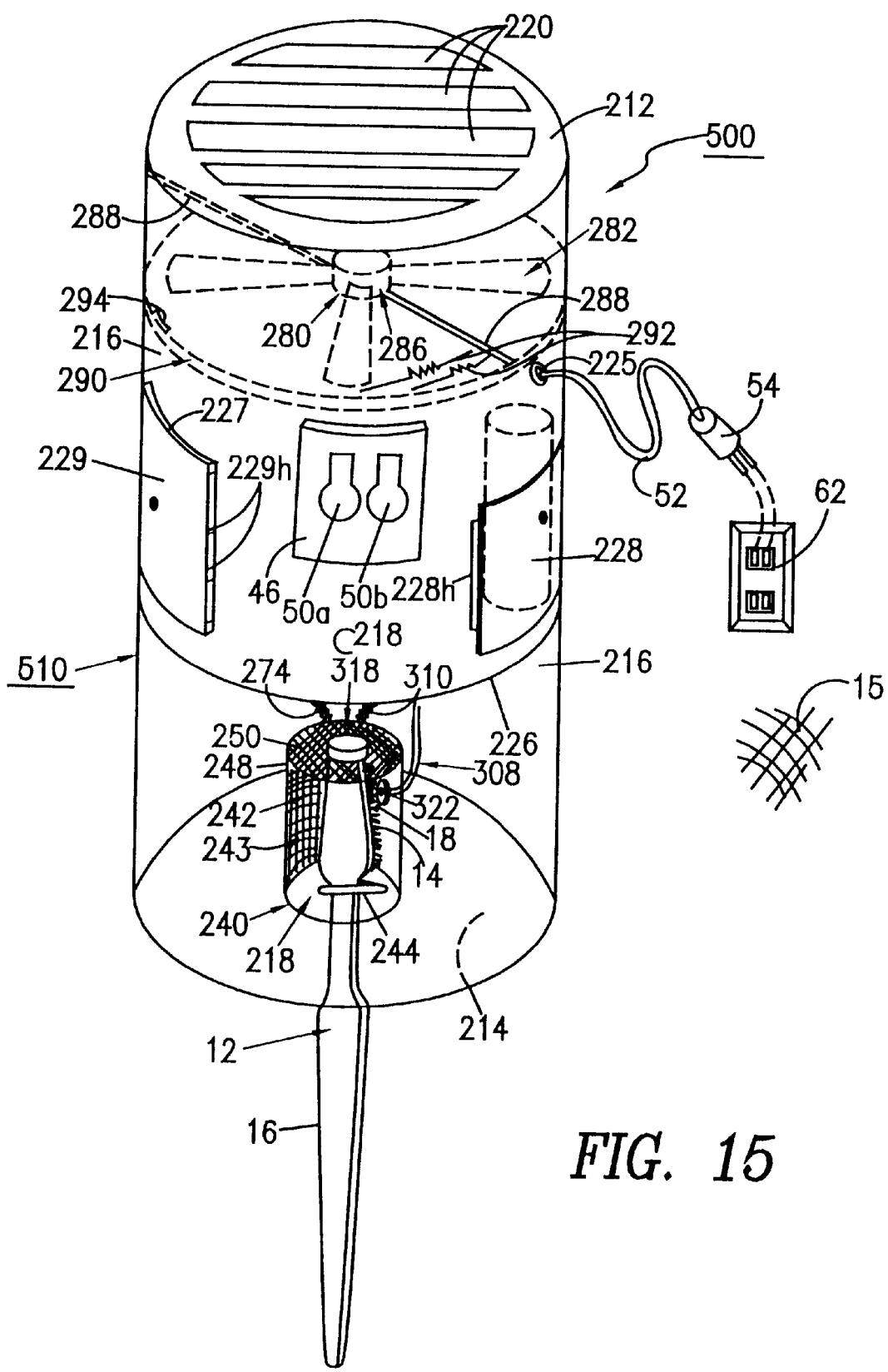
FIG. 15 is a bottom perspective view of the toothbrush sterilization system of the third alternate embodiment of the present invention showing the sterilization device in its assembled state and in operational use.

The toothbrush sterilization system 500 and its component parts of the third alternate embodiment are represented in detail by FIGS. 14 and 15 of the patent drawings. All aspects of the toothbrush sterilization system 500 are the same as the first alternate embodiment of the toothbrush sterilization system 200 except for a mounting bracket 46 having a plurality of keyhole openings 50a to 50d for mounting the sterilization housing 510 onto a wall or on a vertical plane (i.e. tree, tent pole, etc. via screws or hooks) for home use or non-home use, such as camping. Mounting bracket 46 is positioned on the rear section area 218 of the outer curved wall 216, as shown in FIG. 15 of the drawings.

Operation of the Present Invention Preferred and Alternate Embodiments 10 and 400

In operation, the toothbrush sterilization units 10 and 400 of the preferred and second alternate embodiments are readily put into operational use by initially checking the disinfectant reservoir container 102 for the level of disinfectant liquid 18 by visually seeing if the indicator light 105 is "red" for indicating a low level of disinfectant liquid 18 or by opening the reservoir compartment door 56 for visually checking the reservoir level. If more disinfectant liquid 18 is needed, the user simply opens the snap-on cap 104 on the reservoir container 102 and adds more disinfectant liquid 18 to the reservoir container 102 until it is full. Then the user snaps back on cap 104 and closes the reservoir compartment door 56 on the housing 20. Next, the user plugs in the plug 54 with electrical cord 52 thereon to the outlet receptacle 62, as shown in FIGS. 1, 2 and 6 of the drawings, for supplying electrical power to the sterilization unit 10. The sterilization unit 10 is now in operational order to sterilize one or more toothbrushes 12 to a sterile state.

After one or more users have brushed their teeth, using their own toothbrushes 12A and 12B, as depicted in FIG. 5 of the drawings, then each user rinses their toothbrush 12A and 12B in a water rinse to remove any excess toothpaste or debris from their toothbrushes 12A and 12B. Each user then simply inserts their respective toothbrushes 12A and 12B by their handles 16A and 16B into openings 38b and 38c and attach each of the toothbrushes 12A and 12B to holding clips 144b and 144c within docking stations 140B and 140C, respectively. The user then turns each of the bristle-head sections 14A and 14B via handle sections 16A and 16B within holding clips 144b and 144c, respectively, to face inwardly such that each bristle-head sections 14A and 14B are facing atomizer nozzles 132b and 132c within cavity-type housings 142b and 142c, respectively, as shown in FIGS. 1, 2 and 5 of the drawings. Each of the users then releases each handle section 16A and 16B of toothbrushes 12A and 12B in holding clips 144b and 144c, respectively, wherein weight sensor indicators 146b and 146c then signal the PLC circuit chip 60 that bristle-heads 14A and 14B are now ready to be sterilized.

The PLC circuit chip 60 then signals the timer mechanism 70 to start the pumping sequence for discharging the antimicrobial disinfectant liquid spray 18 onto each bristle-head 14A and 14B via atomizer nozzles 132b and 132c, respectively. In the pumping sequence step the disinfectant liquid 18 is pumped from the reservoir container 102 via miniature pump 110, where the disinfectant liquid 18 is then pumped through the opened valve members 124b and 124c, respectively, such that the disinfectant liquid 18 is discharged through atomizer nozzles 132b and 132c as a fine spray mist onto each bristle-head 14A and 14B, respectively. The disinfectant liquid spray 18 is discharged onto the bristle-heads 14A and 14B for a specific length of time (i.e. in the range of 2 to 4 seconds in duration with a preferred duration of 3 seconds). Disinfectant liquid 18 will kill and destroy all microorganisms and viruses that are on bristle-heads 14A and 14B, respectively.

After a short time delay (i.e. 5 to 10 seconds in duration), the PLC circuit chip 60 again signals the timer mechanism 70 to start the drying sequence in the sterilizing of each of the bristle-head sections 14A and 14B of toothbrushes 12A and 12B within docking stations 140B and 140C, respectively. The timer mechanism 70 in turn initiates the start-up of the rotary fan 80, as well as the heating element grid member 90 for drying the disinfectant liquid spray 18 on each of the bristle-heads 14A and 14B within the docking stations 140B and 140C, respectively. In the drying sequence step, ambient air 19 is sucked in through vent openings 36 inwardly through the upper compartment section 32 via rotary fan 80. The ambient air 19 is heated up by the heating elements 92 within grid member 90, such that the ambient air 19 becomes hot enough (i.e. 175° F.) that the hot air 19 begins the drying process on bristle-heads 14A and 14B, respectively. The hot air 19 flows through the porous cavity-type housings 142b and 142c of docking stations 140B and 140C, respectively. This drying process by hot air 19 on each bristle-head 14A and 14B is performed for a specific length of time (i.e. in the range of 30 to 60 seconds duration with a preferred duration of 45 seconds).

The users can increase or decrease the pumping duration or drying duration of timer mechanism 70 via switches or knobs 72 and 76 by changing switch or knob positions 72A, 72B, 78A or 78B, respectively, in order to more efficiently sterilize each of the bristle-heads 14A and 14B within the toothbrush sterilization unit 10 of the preferred embodiment.

After the drying process has been completed and both the rotary fan 80 and heating element grid member 90 are in the "OFF" mode, then indicator lights 150b and 150c light-up "green" for the user in order to indicate that each toothbrush 12A and 12B is dry from the disinfectant liquid spray 18 and is ready for reuse by the user. The toothbrushes remain in housing 20 until they are ready for reuse in order to maintain them in a sterile condition.

When the users are ready to brush their teeth again, at a subsequent time, each user can employ the voice recognition system 160. The user transmits a verbal command, such as "Ken's toothbrush, please" to the voice receiver member 162 which then produces a verbal response "Ken's toothbrush is in docking station number 2 (140B)" via the voice speaker member 164. Then indicator light 150b will start to flash "green" to show the user which toothbrush 12A is to be used.

Alternate Embodiments 200 and 500

In operation, the toothbrush sterilization units 200 and 500 of the alternate embodiments are readily put into operational use by initially checking the reservoir container 302 for the level of disinfectant liquid 18 by opening the reservoir compartment door 228. If more disinfectant liquid 18 is needed, the user simply opens the screw-on cap 306 on the reservoir container 302 and adds more disinfectant liquid 18 to the reservoir container 302 until it is full. The user then screws the cap 306 back on reservoir container 302 and closes the reservoir compartment door 228 on the housing 210. In the next step, the user opens the battery compartment door 229 and checks the power level of the plurality of the batteries 264 within the battery compartment 262 to check for sufficient power of the batteries 264. If the batteries 264 need replacement, the user simply removes the old batteries 264 from battery compartment 262 and replaces them with new batteries 264 and closes the battery compartment door 229 on the housing 210. Next, the user has a choice of power supply, as shown in FIG. 6, of either batteries 264 for using the toothbrush sterilization unit 200 in a portable mode or using the toothbrush sterilization system 200 in a non-portable mode by simply plugging the electrical cord and plug 52 and 54 into an electrical outlet receptacle 62, as shown in FIGS. 7, 8, 10 and 11 of the drawings. The sterilization unit 200 is now in operational order to sterilize a single toothbrush 12 to a sterile state.

After the user has brushed his or her teeth using toothbrush 12, as depicted in FIG. 7 of the drawings, the user then reuses the toothbrush 12 in a water rinse to remove any excess toothpaste or debris from the toothbrush 12. The user then inserts the toothbrush 12 by handle 16 into oval opening 218 of docking station 240 and attaches the handle section 16 within holding clip 244 for holding toothbrush 12 in an upright position, as shown in FIG. 10 of the drawings. The user then turns the bristle-head section 14 via handle 16 within the holding clip 244, such that bristle-head 14 is facing inwardly in order for the atomizer nozzle 322 to spray disinfectant liquid 18 within the cavity-type housing 242, as shown in FIGS. 7, 8 and 10 of the drawings. Bristle-head 14 of toothbrush 12 is now ready to be sterilized within the toothbrush sterilization unit 200 of the alternate embodiment.

In this manual mode, the user simply pushes handle section 16 downwardly so the top 14t of the bristle-head 14 contacts and moves the start-up pump button 314 within cavity-type (well) housing 242 of docking station 240 to move coil spring 310 and 274. Thus, manual activation of pump button 314 then initiates the pumping sequence via coil spring 310 to discharge disinfectant liquid 18 onto bristle-head 14, and also activates timer mechanism 270 via coil spring 274 to start the drying process (after a short time delay of 5 to 10 seconds) of the disinfectant liquid 18 on the bristle-head 14 of toothbrush 12. Timer mechanism 270 also initiates the start-up of the rotary fan 280 and heating element grid member 290 to an "ON" mode. In the pumping sequence step, the disinfectant liquid 18 is manually pumped from the reservoir container 302 via the downward movement of pump head member 304 so that the disinfectant liquid 18 is pumped to and discharged through the atomizer nozzle 322 as a fine spray mist onto the bristle-head 14 of toothbrush 12. Pump head member 304 discharges a specific amount of liquid disinfectant 18 onto the bristle-head 14 (i.e. being in the range of 2 to 4 ml of disinfectant liquid 18 or a preferred amount of 3 ml). Disinfectant liquid 18 will kill and destroy all microorganisms and viruses that are on bristle-head 14 of toothbrush 12.

After a short time delay (i.e. 5 to 10 seconds in duration) the timer mechanism 270 starts the drying sequence in the sterilizing of the bristle-head 14 of toothbrush 12 within docking station 240. The timer mechanism 270 in turn initiates the start-up of the rotary fan 280, as well as the heating element grid member 290 for drying of the disinfectant liquid spray 18 on the bristle-head 14 within the docking station 240. In the drying sequence step, ambient air 19 is sucked in through vent openings 220 upwardly through the lower compartment section 234 via rotary fan 280. The ambient air 19 is heated up by the heating elements 292 within grid member 290, such that the ambient air 19 becomes hot enough (i.e. 175° F.) that the hot air 19 begins the drying process on bristle-head 14. The hot air 19 flows through the porous cavity-type housing 242 of docking station 240. This drying process on bristle-head 14 is performed for a specific length of time (i.e. in the range of 30 to 60 seconds duration with a preferred duration of 45 seconds). It should be noted that timer mechanism 270 is preset for a specific drying time duration.

After the drying process has been completed and both the rotary fan 280 and heating element grid member 290 are in the "OFF" mode, the indicator light 350 will light-up "green" for the user in order to indicate that the single toothbrush 12 is dry from the disinfectant liquid spray 18 and is ready for reuse by the user. The toothbrush 12 remains in housing 210 until they are ready for reuse in order to maintain them in a sterile condition.

Advantages of the Present Invention

Accordingly, an advantage of the present invention is that it provides for a toothbrush sterilization system that incorporates a hot air drying device to be used in conjunction with an anti-microbial spray to effectively sterilize and hold multiple toothbrushes in an ergonomically designed toothbrush holder having a plurality of docking stations therein for use on a wall or counter-top.

Another advantage of the present invention is that it provides for a toothbrush sterilization system that would administer the anti-microbial spray onto the bristle section of the toothbrush automatically or manually in order to decontaminate the toothbrush bristles.

Another advantage of the present invention is that it provides for a toothbrush sterilization system having a docking station for receiving a toothbrush, and an automatic switch for activating a hot air drying device that would effectively dry the disinfectant spray on the bristle head of the toothbrush.

Another advantage of the present invention is that it provides for a toothbrush sterilization system that includes a light indicator by each docking station which signals the user when each toothbrush has dried the disinfectant spray and is ready for reuse.

Another advantage of the present invention is that it provides for a toothbrush sterilization system that includes numbered or color coded docking stations, such that the toothbrush remains in its docking station protected from any airborne bacteria and separated from toothbrushes of other family members which would be contained within their own coded docking station.

Another advantage of the present invention is that it provides for a toothbrush sterilization system that contains voice recognition capabilities to tell each user which toothbrush is theirs when any given toothbrush is removed from its personal docking station.

Another advantage of the present invention is that it provides for a toothbrush sterilization system that is battery operated for portability.

Another advantage of the present invention is that it provides for a toothbrush sterilization system that is lightweight, easy to clean, made from durable plastics or metals, and is easy to use by the consumer.

A further advantage of the present invention is that it provides for a toothbrush sterilization system that can be mass produced in an automated and economical manner and is readily affordable by the consumer.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A toothbrush sterilization unit for sterilizing the bristle-heads of at least two toothbrushes with a disinfectant, comprising:

a) a housing having an interior compartment;
   b) said interior compartment including at least two separate docking stations for receiving one toothbrush in each of said at least two docking stations; each of said at least two docking stations being a separate chamber having means configured for containing the bristle-head of a toothbrush therein;
   c) said housing including means for dispensing a disinfectant on the bristle-heads of said at least two toothbrushes during a dispensing cycle; nozzle means in each of said at least two docking stations for spraying the disinfectant;
   d) said housing including means for drying the disinfectant on the bristle-heads of said at least two toothbrushes during a drying cycle.

2. A toothbrush sterilization unit in accordance with claim 1, wherein said interior compartment includes a plurality of docking stations for receiving a plurality of toothbrushes to be sterilized.

3. A toothbrush sterilization unit in accordance with claim 1, wherein said means for dispensing includes a reservoir of disinfectant, pumping means connected to said reservoir for pumping the disinfectant to said nozzle means for spraying the disinfectant on said bristle-heads of said at least two toothbrushes during said dispensing cycle.

4. A toothbrush sterilization unit in accordance with claim 3, wherein said means for drying the disinfectant on the bristle-heads of said at least two toothbrushes includes means for heating ambient air to provide heated air, and means for blowing the heated air to dry the disinfectant on said bristle-heads of said toothbrushes during said drying cycle.

5. A toothbrush sterilization unit in accordance with claim 4, further including timer means connected to said means for drying for controlling the length of said drying cycle.

6. A toothbrush sterilization unit in accordance with claim 5, wherein said means for heating includes a heating element for heating the ambient air, and wherein said means for blowing the heated air includes a fan.

7. A toothbrush sterilization unit in accordance with claim 3, further including timer means connected to said means for dispensing for controlling the length of said dispensing cycle.

8. A toothbrush sterilization unit in accordance with claim 5, wherein said interior compartment includes a first compartment section having said means for drying, said pumping means and said timer means therein, and a second compartment section having said means for dispensing, said nozzle means for spraying and said at least two docking stations therein.

9. A toothbrush sterilization unit in accordance with claim 8, wherein said second compartment further includes programmable means for controlling, dispensing and drying the disinfectant on the bristle-heads of said at least two toothbrushes.

10. A toothbrush sterilization unit in accordance with claim 9, wherein said programmable means includes a programmable logic controller (PLC) circuit chip having a plurality of transistor elements therein.

11. A toothbrush sterilization unit in accordance with claim 8, wherein first compartment further includes power source means for supplying power to said sterilization unit.

12. A toothbrush sterilization unit in accordance with claim 11, wherein said power source means includes a plug and electrical cord for plugging into an electrical outlet receptacle in order to supply electrical power to said sterilization unit.

13. A toothbrush sterilization unit in accordance with claim 11, wherein said power source means includes a battery compartment for receiving a plurality of batteries therein for supplying power to said sterilization unit.

14. A toothbrush sterilization unit in accordance with claim 3, wherein said housing includes a top wall, a bottom wall, a curved outer wall and a rear wall.

15. A toothbrush sterilization unit in accordance with claim 14, wherein said top wall includes a plurality of air vent openings for receiving ambient air therethrough.

16. A toothbrush sterilization unit in accordance with claim 1, wherein each of said docking stations include an opening in the bottom thereof for receiving a single toothbrush.

17. A toothbrush sterilization unit in accordance with claim 14, wherein said curved outer wall includes a first opening for receiving an electrical cord with a plug therethrough and a second opening for receiving a reservoir door therein.

18. A toothbrush sterilization unit in accordance with claim 14, wherein said rear wall includes mounting means for mounting said sterilization unit on a vertical surface or on a wall.

19. A toothbrush sterilization unit in accordance with claim 3, further including a valve connected to each of said docking stations and control means for controlling said pumping means and each of said valves to open and close and control the supply of disinfectant to each of said nozzle means in said docking stations.

20. A toothbrush sterilization unit in accordance with claim 19, further including timer means for increasing or decreasing the length of time said pumping means operates.

21. A toothbrush sterilization unit in accordance with claim 6, wherein said timer means connected to said means for drying varies the time said fan operates.

22. A toothbrush sterilization unit in accordance with claim 1, wherein said at least two docking stations each include a porous chamber having a holding clip for holding a toothbrush, a weight sensor indicator for sensing the presence of a toothbrush therein, and an opening for receiving said nozzle means therein.

23. A toothbrush sterilization unit in accordance with claim 14, wherein said curved outer wall includes a plurality of circular hole openings, each of said circular hole openings for receiving an indicator light therein for indicating the presence of a sterile toothbrush.

24. A toothbrush sterilization unit in accordance with claim 23, wherein each of said indicator lights includes a lens cover having a color selected from the group consisting of green, yellow, amber, red, blue, orange and white.

25. A toothbrush sterilization unit in accordance with claim 18, wherein said mounting means includes a mounting bracket having a plurality of keyhole openings thereon, for mounting said sterilization unit on a vertical surface or on a wall.

26. A toothbrush sterilization unit in accordance with claim 1, wherein said housing is made from a light-weight, moldable and durable plastic.

27. A toothbrush sterilization unit in accordance with claim 1, wherein said housing is made from a light-weight, formable and durable metal such as aluminum or stainless steel.

28. A toothbrush sterilization unit in accordance with claim 23, further including a voice recognition system in conjunction with said plurality of indicator lights for indicating to each user which toothbrush is theirs when a toothbrush is to be removed from one of said docking stations.

29. A toothbrush sterilization unit in accordance with claim 28, wherein said voice recognition system includes a voice receiving member for receiving incoming voice commands and a voice speaker for transmitting voice messages to the user for indicating which one of said plurality of docking stations contains the user's toothbrush.

30. A toothbrush sterilization unit in accordance with claim 29, wherein said curved outer wall includes a first perforated hole opening area for receiving of said voice receiving member, and a second perforated hole opening area for receiving said voice speaker.

31. A toothbrush sterilization unit in accordance with claim 20, wherein said timer means includes a timing sequence for said pumping means for discharging the disinfectant on the bristle-heads of said toothbrushes for a specific length of time having a range of 2 to 4 seconds in duration.

32. A toothbrush sterilization unit in accordance with claim 20, wherein said timer means includes a timing sequence for said pumping means for discharging the disinfectant on the bristle-heads of said toothbrushes for a specific length of time having a duration of 3 seconds.

33. A toothbrush sterilization unit in accordance with claim 21, wherein said timer means includes a time delay in the range of 5 to 10 seconds in duration before the start-up of said fan and said heating element for the drying cycle for sterilizing the bristle-heads of said toothbrushes.

34. A toothbrush sterilization unit in accordance with claim 21, wherein said timer means includes a timing sequence for said fan and said heating element for the drying the disinfectant on the bristle-heads of said toothbrushes having a range of 30 to 60 seconds in duration.

35. A toothbrush sterilization unit in accordance with claim 21, wherein said timer means includes a timing sequence for said fan and said heating element for the drying the disinfectant on the bristle-heads of toothbrushes having a duration of 45 seconds.

36. A toothbrush sterilization unit in accordance with claim 14, wherein said bottom wall includes mounting means for mounting said housing in an upright position on a counter top.

37. A toothbrush sterilization unit in accordance with claim 36, wherein said mounting means includes a plurality of foot pad members for mounting said housing in an upright position on a counter top.

38. A toothbrush sterilization unit in accordance with claim 2, wherein said plurality of docking stations includes two docking stations.

39. A toothbrush sterilization unit in accordance with claim 2, wherein said plurality of docking stations includes four docking stations.

40. A toothbrush sterilization unit in accordance with claim 1, wherein said nozzle means includes an atomizer nozzle for applying a fine mist spray of disinfectant which evaporates leaving no disinfectant liquid to be collected.

41. A toothbrush sterilization unit in accordance with claim 1, wherein said means for holding the bristle-head of a toothbrush in each of said docking stations includes a holding clip or a holding bracket.

42. A toothbrush sterilization unit in accordance with claim 1, wherein each of said docking stations have an opening on the bottom thereof for receiving a bristle-head of a toothbrush therein, and each of said docking stations are constructed to evaporate the sprayed disinfectant leaving no liquid disinfectant to be collected, and having no liquid collection means in each of said docking stations.

* * * * *